US012607637B2

(12) United States Patent
Diao

(10) Patent No.: US 12,607,637 B2
(45) Date of Patent: Apr. 21, 2026

(54) SUPER-RESOLUTION MORPHOLOGY-CORRELATED DETECTION OF LABILE ZINC

(71) Applicant: University of Cincinnati, Cincinnati, OH (US)

(72) Inventor: Jiajie Diao, Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 632 days.

(21) Appl. No.: 17/927,997

(22) PCT Filed: May 28, 2021

(86) PCT No.: PCT/US2021/034798

§ 371 (c)(1),
(2) Date: Nov. 28, 2022

(87) PCT Pub. No.: WO2021/243176

PCT Pub. Date: Dec. 2, 2021

(65) Prior Publication Data

US 2023/0228761 A1 Jul. 20, 2023

Related U.S. Application Data

(60) Provisional application No. 63/031,260, filed on May 28, 2020.

(51) Int. Cl.

*G01N 33/58* (2006.01)
*G01N 33/84* (2006.01)
*G01N 21/64* (2006.01)
*G01N 31/22* (2006.01)

(52) U.S. Cl.

CPC ........... *G01N 33/582* (2013.01); *G01N 33/84* (2013.01); *G01N 21/6486* (2013.01); *G01N 31/22* (2013.01)

(58) Field of Classification Search

CPC .... G01N 33/582; G01N 33/84; G01N 33/487; G01N 33/20; G01N 31/22; G01N 21/6456; G01N 21/6486; Y10T 436/145555; Y10T 436/17

USPC ......... 436/81, 96, 106, 164, 172; 422/82.05, 422/82.08

See application file for complete search history.

(56) References Cited

U.S. PATENT DOCUMENTS

| | | | | |
|---|---|---|---|---|
| 2012/0271100 A1* | 10/2012 | Woodruff | A61D 19/04 435/7.1 |
| 2016/0030598 A1* | 2/2016 | Radford | A61B 5/4041 546/256 |
| 2020/0131160 A1* | 4/2020 | Li | G01N 21/76 |

OTHER PUBLICATIONS

Zhang et al. New Journal of Chemistry, vol. 42, Oct. 16, 2018, pp. 19245-19251.*
Xu et al. Tetrahedron, vol. 62, Sep. 7, 2006, pp. 10117-10122.*
Lee et al. Sensors and Actuators B: Chemical, vol. 160, Aug. 5, 2011, pp. 1489-1493.*
EP Extended European Search Report dated Jun. 7, 2024 pertaining to EP application No. 21814129.9 filed Dec. 13, 2022, pp. 1-8.
Fan, J. et al. "A Naphthalimide Fluorescent Senor for Zn2+ Based on Photo-induced Electron Transfer" Chemistry Letters, 2004, pp. 1392-1393, vol. 33, No. 10, DOI: 10.1246/cl.2004.1392.
Hamilton, G. et al. "A ratiometric fluorescent hydrogel sensor for zinc(II) based on a two fluorophore approach" New Journal of Chemistry, 2014, pp. 2823-2830, vol. 38, DOI: 10.1039/c4nj00291a.
Lu, C. et al. "Ratiometric and Highly Selective Fluorescent Sensor for Cadmium under Physiological pH Range: A New Strategy to Discriminate Cadmium from Zinc" The Journal of Organic Chemistry, 2007, pp. 3554-3557, vol. 72, DOI: 10.1021/jo070033y.
Xu, Z. et al. "Development of off-on fluorescent probes for heavy and transition metal ions" Chemical Communications, 2010, pp. 1679-1681, vol. 46, DOI: 10.1039/b924503k.
International Search Report mailed on Oct. 13, 2021 in reference to PCT/US2021/34798 filed May 28, 2021.
Written Opinion mailed on Oct. 13, 2021 in reference to PCT/US2021/34798 filed May 28, 2021.
Fang, et al., "Simultaneous Zn2+ tracking in multiple organelles using super-resolution morphology-correlated organelle identification in living cells", Nature Communications, 2021. 12:109, 14 pgs, entire document.
Flynn et al. "Correlation and Prediction of Mass Transport across Membranes I: Influence of Alkyl Chain Length on Flux-Determining Properties of Barrier and Diffusant", Journal of Pharmaceutical Sciences. 1972. vol. 61, No. 6, pp. 838-852, especially: p. 843, col. 2, para 2.
M. Zhang et al. "Simple and efficient delivery of cell impermeable organic fluorescent probes into live cells for live-cell superresolution imaging", Light: Science & Applications. 2019. 8:73, 11 pages, especially: p. 1, col. 1, para 1.
C. Zhang et al. "In vitro and in vivo imaging application of a 1,8-naphthalimide-derived Zn(2+) fluorescent sensor with nuclear envelope penetrability", Chem. Commun. 2013. 49, pp. 11430-11432, especially: abstract; p. 11430, col. 1, para 1; p. 11430, col. 2, para 1; p. 11430, col. 2, 2-4, para 2; p. 11430, Scheme 1, Naph-BPEA-e; p. 11431, Fig. 1; p. 11431, col. 1, para 1; p. 11431, col. 2, para 2; p. 11432, Fig. 2; p. 11432, col. 1, para 1; p. 11432, col. 1, para 2.

* cited by examiner

*Primary Examiner* — Maureen Wallenhorst
(74) *Attorney, Agent, or Firm* — DINSMORE & SHOHL LLP

(57) ABSTRACT

A method for detecting labile zinc ($Zn^{2+}$) in a biological material is provided herein, the method including: (a) contacting the biological material with a composition including NapBu-BPEA; and (b) imaging the biological material via molecular fluorescence imaging to detect the labile zinc in the biological material. Also provided herein are methods for morphology-correlated detection of labile zinc localization in a subcellular organelle of a living cell and methods for tracking a change in labile zinc localization in a biological material.

23 Claims, 10 Drawing Sheets

SUPER-RESOLUTION MORPHOLOGY-CORRELATED DETECTION OF LABILE ZINC

CROSS-REFERENCE TO RELATED APPLICATIONS

This application is a § 371 National Stage Application of International Application Serial No. PCT/US2021/034798, filed May 28, 2021, and claims the benefit of U.S. Provisional Application Ser. No. 63/031,260, filed May 28, 2020, the entire disclosures of which are incorporated herein by reference.

TECHNICAL FIELD

The present disclosure relates to the field of labile zinc imaging. Specifically, the present disclosure relates to methods for detection and visualization of labile zinc in biological materials.

BACKGROUND

Zinc homeostasis, including labile $Zn^{2+}$ fluctuation, is closely associated with many physiological processes and disease pathologies. As the newly proposed "second messenger," labile $Zn^{2+}$ is involved in both inter- and intracellular signal regulation and transmission, and new phenomena for labile $Zn^{2+}$-associated signal transduction, such as zinc sparks and zinc waves, have been observed using fluorescence imaging. Except for various organelles having different $Zn^{2+}$ levels and dynamics, many physiological processes involving multiple organelles are also associated with $Zn^{2+}$ fluctuation. In particular, a growing body of evidence suggests that $Zn^{2+}$ is pivotal to autophagy and autophagy can prompt significant changes in intracellular $Zn^{2+}$. As a dynamic process for cells to degrade and recycle proteins and senescent organelles to overcome stressful conditions, autophagy is associated with aging, neurodegenerative diseases, diabetes, and fatty liver disease, and is a potential target for diagnosis and treatment. It is therefore important to determine $Zn^{2+}$ signaling relationships among organelles during autophagy and other cellular processes.

As scientists have begun to better understand the role of labile zinc in key cellular functions, a need has emerged for improved methods for detecting and visualizing labile zinc in biological materials.

SUMMARY

Accordingly, provided herein are improved methods for detecting, imaging, and tracking labile zinc in biological materials, including living cells and organoids. The presently disclosed methods permit nanometer-level detection of labile zinc and correlation with morphological features of organelles to visualize the distribution of labile zinc in the biological material. Advantageously, the present methods do not require organelle-specific targeting molecules or co-localization with additional dyes.

In one embodiment, a method for detecting labile zinc ($Zn^{2+}$) in a biological material is provided, the method comprising: (a) contacting the biological material with a composition comprising NapBu-BPEA; and (b) imaging the biological material via molecular fluorescence imaging to detect the labile zinc in the biological material.

In another embodiment, a method for morphology-correlated detection of labile zinc localization in a subcellular organelle of a living cell is provided, the method comprising: (a) contacting the cell with a composition comprising NapBu-BPEA; (b) imaging the cell via super-resolution imaging to visualize a distribution of labile zinc in the cell; and (c) correlating the distribution of labile zinc in the cell with at least one morphological feature of the subcellular organelle to determine labile zinc localization in the subcellular organelle.

In another embodiment, a method of tracking a change in labile zinc localization in a biological material is provided, the method comprising: (a) contacting the biological material with a composition comprising NapBu-BPEA; (b) imaging the biological material via super-resolution imaging to detect the labile zinc in the biological material; (c) repeating step (b) at determined time intervals and comparing obtained super-resolution imaging data to track the change in labile zinc localization in the biological material over time.

These and other objects, features, embodiments, and advantages will become apparent to those of ordinary skill in the art from a reading of the following detailed description and the appended claims.

DETAILED DESCRIPTION

Figure 1:
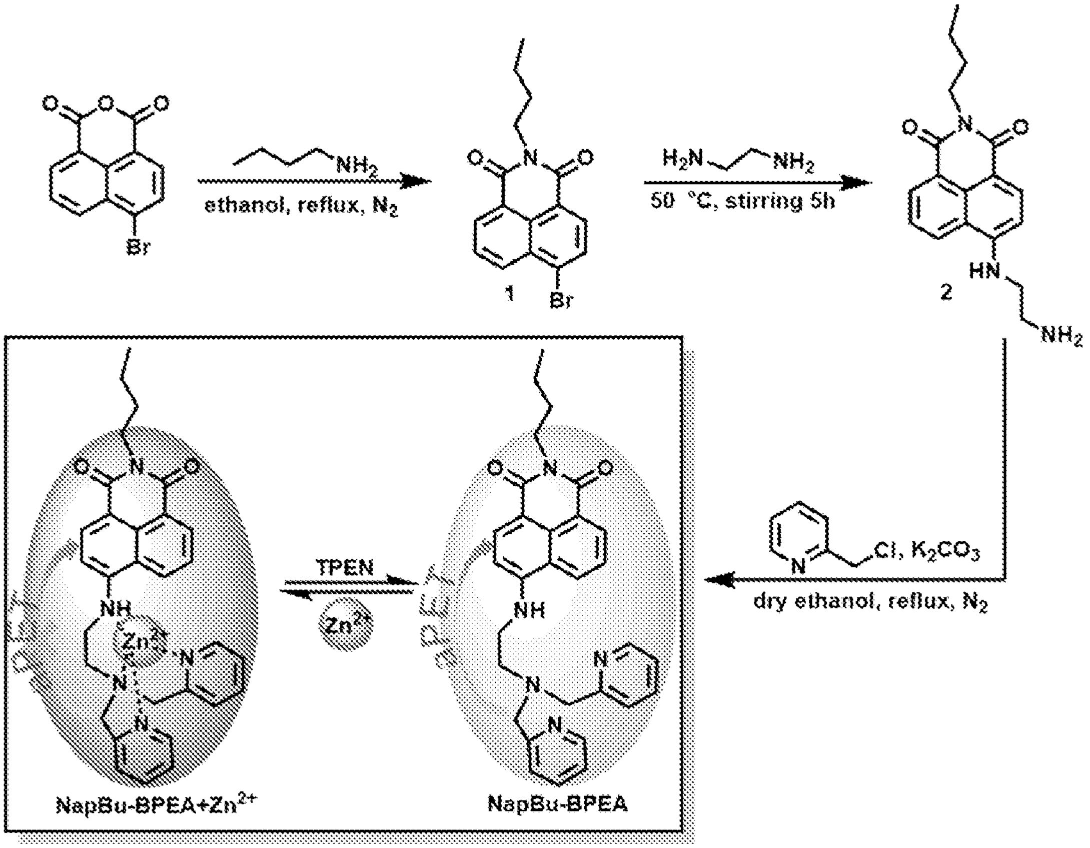
FIG. 1 is an illustration showing the synthesis and reversible response process of NapBu-BPEA.

The details of embodiments of the presently-disclosed subject matter are set forth in this document. Modifications to embodiments described in this document, and other embodiments, will be evident to those of ordinary skill in the art after a study of the information provided in this document.

While the following terms are believed to be well understood in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

As used in this specification and the appended claims, the singular forms "a," "an" and "the" include plural references unless the content clearly dictates otherwise.

Zinc is a key micronutrient for mammals and plays a role in a variety of cellular pathways. Labile zinc functions in cells as a signaling molecule and as a component of many proteins and enzymes. "Labile zinc," as used herein, refers to intracellular $Zn^{2+}$. $Zn^{2+}$ is the most abundant intracellular metal ion found in the cytosol, vesicles, nucleus, and organelles of mammalian cells.

"Biological material," as used herein, refers to living cells, tissues, organoids, and organisms. In embodiments, the biological material is mammalian. In specific embodiments, biological materials for use in the disclosed methods are selected from the group consisting of living cells, organoids, and combinations thereof.

"NapBu-BPEA" refers to a fluorescent probe having the following structure:

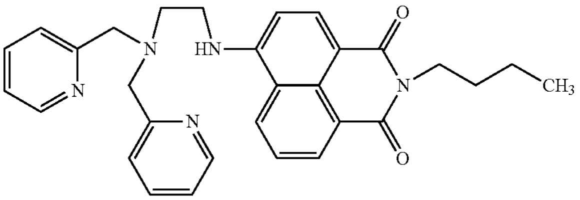 [SMILES: CCCCN1C(=O)c2cccc3c(NCCN(Cc4ccccn4)Cc4ccccn4)ccc(c23)C1=O]

2,4-(bis(pyridin-2-ylmethyl)aminoethyl)amino-N-n-butyl-1,8-naphthalimide. NapBu-BPEA comprises a N,N'-bis(pyridin-2-ylmethyl)ethane-1,2-diamine (BPEA) moiety bound to 1,8-naphthalimide (Nap) and modified with a butyl group (Bu).

"Molecular fluorescence imaging" refers to imaging techniques that leverage the optical emissions of molecules that have been excited to higher energy levels by absorption of electromagnetic radiation. Generally, molecular fluorescence imaging uses fluorophore-labeled dyes or proteins, which may be used for either direct or indirect detection of a target. Molecular fluorescence imaging has application in observing the dynamics of gene expression, protein expression, and molecular interactions in living cells. Various molecular fluorescence techniques are known in the art and suitable for use in the present methods.

"Super-resolution imaging" refers to a class of techniques that permits imaging of subcellular structures with a spatial resolution beyond the diffraction limit of conventional light microscopy. See Zhang, et al., *Simple and efficient delivery of cell-impermeable organic fluorescent probes into live cells for live-cell superresolution imaging, Light Sci. Appl.* 8: 73 (2019). Various super-resolution imaging techniques are known in the art and include, but are not limited to, structured illumination microscopy (SIM), stimulated emission depletion (STED) microscopy, ground state depletion (GSD) microscopy, photo-activated localization microscopy (PALM), stochastic optical reconstruction microscopy (STORM), and the like. In specific embodiments of the present disclosure, the super-resolution imaging technique employed is SIM.

"Structured illumination microscopy" (SIM) provides enhanced spatial resolution and involves illuminating a sample with patterned light and using software to analyze the information in Moiré fringes outside the normal range of observation. Reconstruction software deciphers the images at about 2-fold higher resolution than the diffraction limit, or ~100 nm. SIM is suitable for imaging thicker sections, for 3D imaging, and for live-cell imaging. See Feiner-Gracia, et al., Smart *Nanoparticles for Biomedicine, Advanced Optical Microscopy Techniques for the Investigation of Cell-Nanoparticle Interactions*, Chapter 15 (2018).

The present disclosure is directed to novel methods of imaging labile zinc in biological materials with high spatial resolution at the nanometer scale. These methods open new avenues for the study of molecular mechanisms in biological materials, including living cells and organoids.

For dynamic tracking and quantification of labile zinc, molecular fluorescence imaging is a reliable method for rapidly tracking biological materials in situ, particularly due to its high sensitivity, selectivity, rapid response, and non-invasiveness. The presently disclosed methods employ molecular fluorescence imaging to track the temporal and spatial distribution of zinc in cells, subcellular organelles, and organoids. Because subcellular organelles are the units that perform various physiological functions in cells, it is pivotal to detect changes in zinc levels in organelles during autophagy. However, due to the limitations of fluorescent imaging resolution, detecting zinc dynamics in organelles has remained a challenge.

Although optical microscopy presents several advantages in detecting the intracellular content of bioanalytes, its resolution of approximately 250 nm limits its applicability. In recent years, the development of super-resolution imaging technology has overcome the shortcomings of the diffraction limit of traditional optical technology and been used to perform imaging once deemed impossible. Structured illumination microscopy (SIM), having a spatial resolution of approximately 100 nm, is a particularly favorable option for live cell imaging.

Because small molecular probes offer numerous advantages—large-scale synthesis, simple labeling, tunable wavelengths, and good repeatability, to name a few—small molecular zinc fluorescent probes have become reliable candidates for super-resolution imaging. However, constructing such probes continues to present several setbacks, including frequent photobleaching and low fluorescence quantum yields. For the purpose of biological imaging, naphthalimide (Nap) fluorophores afford a simple structure and high molar extinction coefficients that make them exceptional as probes. Exhibiting a large degree of conjugation, strong rigidity, and, in turn, a low probability of nonradiative transition, the molecular structure of Nap fluorophores affords good photostability and facilitates high fluorescence quantum yields. Nap fluorophores have a lower imaging background signal and favor the 3D super-resolution imaging of large objects. Moreover, the multiple derivative sites of their structure is conducive to introduce organelle-targeting groups to realize the detection of biological species at the level of organelles. For that reason, a variety of specific subcellular organelle-targeting probes have been developed, through modified targeting groups. However, adding targeting groups requires multiple modification sites, which limits the pool of suitable agents. Moreover, because some targeting groups cannot achieve the desired targeting effect, they may alter the imaging performance and the probe's specificity. Thus, it is desirable to develop a method for detecting subcellular organelles using fluorescent probes without the need to introduce organelle-targeting groups.

Based on past successes in the super-resolution imaging of the dynamics of subcellular organelles, it is currently possible to differentiate typical subcellular organelles by morphological features, including rod-shaped mitochondria with cristae, punctate lysosomes, and reticular endoplasmic reticulum. The presently disclosed methods combine the fluorescent distribution of NapBu-BPEA with the morphological features of organelles revealed by super-resolution imaging to provide morphology-correlated detection (MCoD) and determine the localized level of biological species of subcellular organelles, without the use of targeting groups.

NapBu-BPEA has been developed for the super-resolution imaging of labile zinc with a spatial resolution peaking at about 100 nm. By correlating the super-resolution MCoD with the change in ion levels indicated by NapBu-BPEA, the present methods achieve pan-cell zinc detection for individual subcellular organelles via the use of only one probe. Further, NapBu-BPEA has been used to image organoids, which provides a practical basis for studying Zn-related chemical biology in complex biological systems.

NapBu-BPEA is a $Zn^{2+}$-selective, reversible, turn-on response fluorescence sensor with a low detection limit and strong binding ability that can be applied to map whole intracellular organelles in living cells except nuclei. By using NapBu-BPEA, it was observed that CCCP-induced damaged autophagy increased intracellular $Zn^{2+}$, which would transform into autophagosomes. NapBu-BPEA permits monitoring of the accumulation and fluctuation of intracellular concentrations of labile zinc under different conditions of induced autophagy.

Accordingly, in one embodiment, a method for detecting labile zinc ($Zn^{2+}$) in a biological material is provided, the method comprising: (a) contacting the biological material with a composition comprising NapBu-BPEA; and (b) imaging the biological material via molecular fluorescence imaging to detect the labile zinc in the biological material. In specific embodiments, the molecular fluorescence imaging technique comprises super-resolution imaging. Various super-resolution imaging methods are known in the art and suitable for use in the disclosed methods. In embodiments, the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM). In a very specific embodiment, the super-resolution imaging technique is structured illumination microscopy (SIM). Advantageously, SIM provides an enhanced spatial resolution peak of about 100 nm. In embodiments, the molecular fluorescence imaging produces imaging data captured digitally or photographically.

In embodiments, detecting the labile zinc in a biological material comprises visualizing a distribution of labile zinc in the biological material. In embodiments, the method further comprises correlating the distribution of labile zinc in the biological material with a morphological feature of a subcellular organelle to determine labile zinc localization in the subcellular organelle. In a specific embodiment, the morphological feature of the subcellular organelle is selected from the group consisting of shape, structure, size, and combinations thereof.

The presently disclosed methods are suitable for imaging a variety of biological materials. In embodiments, the biological materials comprise organoids, living cells, or subcellular organelles. In embodiments, the biological material is in situ or in vivo.

Advantageously, the presently disclosed methods employ the fluorophore NapBu-BPEA, which does not comprise a specific subcellular organelle-targeting group. Moreover, in embodiments, the presently disclosed methods do not require co-localization with a second dye to correlate the distribution of labile zinc in the biological material with a morphological feature of a subcellular structure, such as an organelle.

In embodiments of the disclosed methods, the NapBu-BPEA binds $Zn^{2+}$ in a 1:1 ratio. In embodiments, the NapBu-BPEA binds $Zn^{2+}$ reversibly.

Optionally, the methods disclosed herein further comprise quantifying the labile zinc in the biological material based on the obtained imaging data. Such quantification may be accomplished using methods known in the art.

In another embodiment, a method for morphology-correlated detection of labile zinc ($Zn^{2+}$) localization in a subcellular organelle of a living cell is provided, the method comprising: (a) contacting the cell with a composition comprising NapBu-BPEA; (b) imaging the cell via super-resolution imaging to visualize a distribution of labile zinc in the cell; and (c) correlating the distribution of labile zinc in the cell with at least one morphological feature of the subcellular organelle to determine labile zinc localization in the subcellular organelle. In further embodiments, the method additionally comprises (d) repeating steps (b) and (c) at determined time intervals and comparing obtained super-resolution imaging data obtained at the determined time intervals to track a change in labile zinc localization in the subcellular organelle over time.

Determined time intervals may be selected by the skilled artisan. In embodiments, the time intervals may be measured by days, hours, minutes, or seconds. In embodiments, the time intervals range in duration from about 1 second to about 1 hour. That is, in embodiments, the biological material is imaged at time intervals ranging from about 1 second to about 1 hour. For example, in a specific embodiment, a biological material may be imaged according to the present methods every 1 minute, every 2 minutes, every 3 minutes, every 4 minutes, every 5 minutes, and so on, for a duration of time selected by the skilled person. In embodiments, the time interval can be any duration of time suitable to image changes in $Zn^{2+}$ in a biological material.

In embodiments, the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM). In a very specific embodiment, the super-resolution imaging technique is structured illumination microscopy (SIM). Advantageously, SIM provides an enhanced spatial resolution peak of about 100 nm.

The presently disclosed methods are suitable for imaging a variety of biological materials. In embodiments, the biological material comprises an organoid, a living cell, or a subcellular organelle. In embodiments, the biological material is in situ or in vivo.

Advantageously, the presently disclosed methods employ the fluorophore NapBu-BPEA, which does not comprise a specific subcellular organelle-targeting group. Moreover, in embodiments, the presently disclosed methods do not require co-localization with a second dye to correlate the distribution of labile zinc in the biological material with a morphological feature of a subcellular structure, such as an organelle. In embodiments, the morphological feature of the subcellular organelle is selected from the group consisting of shape, structure, size, and combinations thereof. In specific embodiments, identifiable morphological features include, but are not limited to, the rod-like shape of mitochondria; the cristae (folded inner membranes) of mitochondria; the punctate appearance of lysosomes; and the reticular appearance of the endoplasmic reticulum, comprising a network of interconnected flattened membrane sacs and/or tubules. Such morphological features are readily distinguishable by the methods disclosed herein.

In embodiments of the disclosed methods, the NapBu-BPEA binds $Zn^{2+}$ in a 1:1 ratio. In embodiments, the NapBu-BPEA binds $Zn^{2+}$ reversibly.

Optionally, the methods disclosed herein further comprise quantifying the labile zinc in the biological material based on the obtained imaging data. Such quantification may be accomplished using methods known in the art.

Advantageously, the presently disclosed methods employ the fluorophore NapBu-BPEA, which does not comprise a specific subcellular organelle-targeting group. Moreover, in embodiments, the presently disclosed methods do not require co-localization with a second dye to correlate the distribution of labile zinc in the biological material with a morphological feature of a subcellular structure, such as an organelle.

In still another embodiment, a method of tracking a change in labile zinc ($Zn^{2+}$) localization in a biological material, the method comprising: (a) contacting the biological material with a composition comprising NapBu-BPEA; (b) imaging the biological material via super-resolution imaging to detect the labile zinc in the biological material; and (c) repeating step (b) at determined time intervals and comparing obtained super-resolution imaging data to track the change in labile zinc localization in the biological material over time.

In embodiments, the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM). In a very specific embodiment, the super-resolution imaging technique is structured illumination microscopy (SIM). Advantageously, SIM provides an enhanced spatial resolution peak of about 100 nm.

In embodiments, the biological material is a cell or an organoid. In embodiments, the NapBu-BPEA does not comprise a specific subcellular organelle-targeting group.

Although an organelle-specific second fluorophore is not required to achieve nanometer-level imaging sufficient to distinguish organelles by the present methods, in embodiments, the skilled artisan may wish to pair NapBu-BPEA with a second fluorophore targeted to one or more specific organelles. Accordingly, in embodiments, the methods set forth herein may include contacting the biological sample with a second fluorophore and imaging the biological material to visualize both NapBu-BPEA and the second fluorophore. Suitable second fluorophores include, but are not limited to, MitoTracker™ Green FM (MTG), MitoTracker™ DeepRed FM (MTDR), Lysolracker™ Red DND-99 (LTR), ER-Tracker™ Red, Hoechst 33258, and the like.

EXAMPLES

The following examples are given by way of illustration are not intended to limit the scope of the disclosure.

Example 1

Materials and Methods

Materials and Instrument

All solvents and reagents are of analytical grade and used without further purification. 4-bromo-1,8-naphthalic anhydride, n-butylamine, ethylenediamine, picolyl chloride and $Ru(bpy)_3^{2+}$ were purchased from Energy Chemical Inc. (Shanghai, China). KCl, $CaCl_2$, $MgCl_2$, NaCl, $FeSO_4$, $FeCl_3$, $Zn(NO_3)_2$, $NiCl_2$, $CdCl_2$, MnC12, BaC12, CrC13, $Al_3(SO_4)_2$ and $Pb(NO_3)_2$ were purchased from Sinopharm Chemical Reagent (Nanjing, China). Carbonyl cyanide m-chlorophenylhydrazone (CCCP), ethylenebis (oxyethylenenitrilo) tetraacetic acid (EGTA) and 2-[4-(2-hydroxyethyl)-1-piperazinyl]ethanesulfonic acid (HEPES) were purchased from Sigma (Shanghai, China). Pyrithione sodium salt, N,N,N',N'-Tetrakis (2-pyridylmethyl) ethylenediamine were obtained from Fisher Scientific Inc. (Ohio, USA). Mitolracker™ Green FM (MTG), Mitolracker™ DeepRed FM, Lysolracker™ Red DND-99 (LTR), ER-Tracker™ Red and Hoechst 33258 were purchased from Invitrogen (Ohio, USA). Autophagosome Detection dye (DAPRed) and Cytoxicity LDH Assay Kit-WST were purchased from Dojindo (Washington, USA). The cell culture medium, Dulbecco's Modified Eagle Medium (DMEM) and Earle's Balanced Salt Solution (EBSS, calcium, magnesium, phenol red) were purchased from Gibco (Ohio, USA).

The $^{1}H$ NMR and $^{13}C$ NMR spectra were determined with a 400 M Bruker spectrometer with TMS as internal standard. High-Resolution Mass spectrometric data were recorded on an Agilent 6540 Q-TOF mass spectrometer. The UV-Vis and fluorescence spectra were performed on PerkinElmer Lambda 35 spectrophotometer and Horiba FM-4 fluorophotometer. The cell imaging was carried out by Nikon N-SIM system.

Spectroscopic Study

The stock solution of NapBu-BPEA was prepared with DMSO of HPLC pure grade to make the concentration as 10 mM, and frozen after packing at −20° C. The sample solutions were diluted to the final concentration as 10 μM with 3 mL HEPES buffer (50 mM, 100 mM $KNO_3$, 10% DMSO, pH 7.2) in quartz cuvettes with 1 cm path lengths. The fluorescent spectra were recorded upon the excitation of 450 nm.

The $Zn^{2+}$ titration spectra were recorded by adding in aliquots $Zn^{2+}$ solution from 0 to 15 μM into the NapBu-BPEA solution (10 μM). The detection limit of NapBu-BPEA was determined by collecting the fluorescence spectra of NapBu-BPEA for 6 times to obtain the background noise (a). The probe's fluorescent sensing selectivity of NapBu-BPEA was recorded after adding metal cation (1000 eq $K^+$, $Na^+$, $Ca^{2+}$, $Mg^{2+}$; 1 eq $Cd^{2+}$, $Ni^{2+}$, $Cr^{3+}$, $Pb^{2+}$, $Al^{3+}$, $Co^{2+}$, $Fe^{2+}$, $Fe^{3+}$, $Ba^{2+}$, $Mn^{2+}$) to the NapBu-BPEA solution. The fluorescence quantum yields were determined by using $Ru(bpy)_3^{2+}$ ($\Phi$=0.04) in DMSO/HEPES (v:v, 1:9)($\lambda_{ex}$=450 nm) as the reference. To determine binding constant, various amounts of $Zn(NO_3)_2$ (0~9 mM) were added to NapBu-BPEA solution buffered with DMSO/HEPES (50 mM, pH 7.21, 100 mM $KNO_3$) containing 10 mM EGTA. The pH stability was measured by recording the fluorescence spectra of NapBu-BPEA solution in the presence of $Zn^{2+}$ at different pH adjusted with KOH and HCl.

Cell Culture

Wild-type, FIP200 and ATG13 KO HeLa cell lines were gifted from Dr. Jun-Lin Guan's lab (University of Cincinnati). Cells were cultured in DMEM supplemented 10% FBS and 100 U/mL penicillin-streptomycin (Gibco) in 5% $CO_2$ incubator at 37° C.

Organoid Culture

Human induced pluripotent stem cells (iPSCs) were differentiated into foregut using previously described method. In brief, hiPSCs were detached by Accutase (Thermo Fisher Scientific Inc., MA, USA) and were seeded on Laminin coated tissue culture plate with 100,000 cells/$cm^2$. Medium was changed to RPMI 1640 medium (Life Technologies) containing 100 ng/mL Activin A (R&D Systems) and 50 ng/mL bone morphogenetic protein 4 (BMP4; R&D Systems) at day 1, 100 ng/mL Activin A and 0.2% fetal calf serum (FCS; Thermo Fisher Scientific Inc.) at day 2, and 100 ng/mL Activin A and 2% FCS at day 3. On day 4-6, cells were cultured in Advanced DMEM/F12 (Thermo Fisher Scientific Inc.) with B27 (Life Technologies) and N2 (Gibco, CA, USA) containing 500 ng/mL fibroblast growth factor (FGF4; R&D Systems) and 3μM CHIR99021 (Stemgent, MA, USA). Cells were maintained at 37° C. in 5% $CO_2$ with 95% air and the medium was replaced every day. The foregut cells were detached by Accutase and then centrifuged at 1200 rpm for 3 min. Cells were resuspended in Matrigel (Corning, In., NY, USA). A total of 100,000 cells were embedded in 5 μL Matrigel drop on the dishes in organoid formation media with 5 factors for 4 days. After organoid formation, the media was switched to liver specification media for 4 days. After the liver specification step, organoids were harvested from Matrigel by scratching and pipetting. Then organoids were re-embedded in Matrigel on the Ultra-low attached plate (Corning) in liver maturation media for 10 days. Cultures for HLO induction were maintained at 37° C. in 5% $CO_2$ with 95% air and the medium was added every 2 days.

Nikon SIM Super-Resolution Imaging

The SIM images were acquired using a Nikon N-SIM system. The blue imaging channel for Hoechst 33258 with emission bandwidth at 420-495 nm upon excitation at 405 nm, the green imaging channel for NapBu-BPEA with emission bandwidth at 500-550 nm upon excitation at 488 nm, the red imaging channel for ER-Tracker Red, LysoTracker Red and DAPRed with emission bandwidth at 570-640 nm upon excitation at 561 nm, the magenta imaging channel for MitoTracker Deep Red with emission bandwidth at 660-735 nm upon excitation at 640 nm were utilized. The imaging data analysis and thermal map construction were performed via analysis with ImageJ.

The co-localization experiments were performed with a dual-channel mode. HeLa cells were stained by NapBu-BPEA (10 μM, 1 h) and then incubated with Mito-marker Deep Red (0.5 μM, 30 min), Lysotracker Red (0.1 μM, 30 min), ER-Tracker Red (1 μM, 30 min), and Hoechst 33258 (1 μg/mL, 30 min), respectively. The Pearson's correlation coefficient was calculated using Cellprofiler with co-localization module.

The intracellular $Zn^{2+}$ level in autophagy was imaged in HeLa cells. Prior to CCCP (10 μM, 24 h) or EBSS treatment (10 μM, 24 h), the cells were stained with DAPRed (1 μM, 30 min). The cells were finally stained by NapBu-BPEA (10 μM, 1 h) before SIM imaging.

The fresh organoids were transferred into petri dish. After 10 μM CCCP treatment for 24 h, the organoids were incubated with 10 μM NapBu—BPEA for 2 h. Then the organoids were imaged with z stack at different depths.

Cell Viability Determination Via WST Assay

The suspension of HeLa cells diluted with 50 μL DMEM was plated into 96-well plate. The inoculated cells were pre-cultured overnight in 96-well plate and replaced with a new 50 μL DMEM. 50 μL DMEM containing different concentrations of NapBu-BPEA was added and cultured in $CO_2$ incubator at 37° C. for 24 h. After 10 μL lysis buffer was added to the high contrast wells, 30 min was cultured in the $CO_2$ incubator at 37° C. After 100 μL working solution was added to each well, it was cultured for 0.5 h under dark and room temperature. After 50 μL stop solution was added to each well, the absorbance of 490 nm was determined immediately by a microplate reader (Thermomax, Molecular Devices).

Data Analysis

All data were analyzed and statistically calculated using Microsoft Excel 2016 software (Microsoft, Redmond, WA). The results are expressed as mean±standard deviation (SD) unless otherwise stated. The statistical differences between the experimental groups were analyzed by double-tailed Student's t-test. When $p<0.05$, it was considered to have statistical significance. All statistical graphs were performed using Origin 2016 (OriginLab Corporation, MA, USA).

Statistics and Reproducibility

Each experiment was repeated at least three times independently with similar results. All images shown are representative results from biological replicates.

Example 2

Design, Synthesis, and Characterization of NapBu-BPEA

The $Zn^{2+}$ fluorescent probe NapBu-BPEA was rationally grafted from a Nap fluorescent platform onto a N,N'-bis (pyridin-2-ylmethyl)ethane-1,2-diamine (BPEA) moiety, which is often used as a $Zn^{2+}$ chelator (FIG. 1). Nap fluorophore was selected due to its favorable optical stability, high extinction coefficient, and high fluorescence quantum yields. Using ChemDraw's predictive algorithms, the lipophilic parameter (logP) of NapBu-BPEA was predicted to be 4.97, which is significantly greater than that of another $Zn^{2+}$ probe, Naph-BPEA (i.e., 2.61). The intermediate compounds and target compound were characterized by $^{1}H$ spectra, $^{13}C$ spectra, and high-resolution mass spectrometry (FIGS. 2-6).

Synthesis of 4-bromo-N-n-butyl-1,8-naphthalimide (1): n-butylamine (0.516 g, 7.05 mmol) was added to 4-bromo-1,8-naphthalic anhydride (0.661 g, 2.3 mmol) dissolved in ethanol (30 mL) and mixed in 50 mL three-necked flask. Then the mixture was stirred and refluxed at 90° C. under $N_2$ for 4 h. After the reaction finished and cooled to room temperature, the mixture was filtered and washed with ethanol (5 mL×3). The residue was collected and dried as light yellow power in 63.4% yield (502 mg). $^{1}H$ NMR (400 MHz, Chloroform-d) δ 8.66 (dd, J=7.3, 1.1 Hz, 1H), 8.57 (dd, J=8.5, 1.2 Hz, 1H), 8.42 (d, J=7.8 Hz, 1H), 8.04 (d, J=7.9 Hz, 1H), 7.85 (dd, J=8.5, 7.3 Hz, 1H), 4.24-4.06 (m, 2H), 1.83-1.62 (m, 2H), 1.52-1.34 (m, 2H), 0.98 (t, J=7.3 Hz, 3H).

Synthesis of N-n-butyl-4-(aminoethylene) amino-1,8-naphthalimide (2): 1 g (3.00 mmol) compound 1 and 6.0 mL (90 mmol) ethylenediamine were added in a 10 mL three-necked flask. After continuous stirring at 50° C. for 5 h, the mixture was cooled and poured into 100 mL of ice water. Then the precipitate was collected by filtration, washed with water, and dried to 64% yield (609 mg). $^{1}H$ NMR (400 MHz, Chloroform-d) δ 8.59 (dd, J=7.3, 1.1 Hz, 1H), 8.47 (d, J=8.4 Hz, 1H), 8.17 (dd, J=8.5, 1.1 Hz, 1H), 7.63 (dd, J=8.4, 7.3 Hz, 1H), 6.71 (d, J=8.5 Hz, 1H), 6.14 (s, 1H), 4.21-4.12 (m, 2H), 3.42 (q, J=5.3 Hz, 2H), 3.18 (dd, J=6.7, 4.9 Hz, 2H), 1.79-1.69 (m, 2H), 1.51-1.38 (m, 2H), 0.97 (t, J=7.3 Hz, 3H).

Synthesis of 2,4-(bis(pyridin-2-ylmethyeaminoethy-pamino-N-n-butyl-1,8-naphthalimide (NapBu-BPEA): 200 mg (0.64 mmol) compound 2 were dissolved in 20 mL dry ethanol. The mixture was stirred and refluxed for 10 hours under $N_2$. The reaction process was monitored by TLC. The solvent was evaporated under reduced pressure, once the reaction was completed. The crude product was purified by silica gel column chromatography ($CH_2Cl_2$: MeOH=20:1) to obtain a yellow solid in 24.6% yield (70 mg). $^{1}H$ NMR (400 MHz, Methanol-$d_4$) δ 8.59 (dd, J=8.4, 1.2 Hz, 1H), 8.50 (d, J=7.3 Hz, 1H), 8.42 (dd, J=5.0, 1.3 Hz, 2H), 8.17 (d, J=8.5 Hz, 1H), 7.68 (dd, J=8.4, 7.3 Hz, 1H), 7.51-7.47 (m, 4H), 7.14 (ddd, J=6.6, 5.2, 2.4 Hz, 2H), 6.51 (d, J=8.5 Hz, 1H), 4.15-4.03 (m, 2H), 3.88 (s, 4H), 3.52 (t, J=5.9 Hz, 2H), 2.92 (t, J=5.9 Hz, 2H), 1.67 (tt, J=8.0, 6.4 Hz, 2H), 1.42 (q, J=7.5 Hz, 2H), 0.99 (t, J=7.3 Hz, 3H). $^{13}C$ NMR (101 MHz, Methanol-$d_4$) δ 166.25, 165.72, 160.27, 152.30, 149.61, 138.51, 135.86, 132.22, 131.27, 129.50, 125.49, 125.25, 123.79, 123.46, 122.00, 109.23, 105.12, 61.16, 53.19, 49.68, 49.54, 49.47, 49.32, 49.25, 49.04, 48.83, 48.69, 48.62, 48.40, 41.88, 40.84, 31.43, 21.42, 14.28. HR-MS(positive mode): Calcd. 494.2551, Found. 494.2649.

Example 3

Spectral Behavior of NapBu-BPEA in Aqueous Solution

Figure 7:
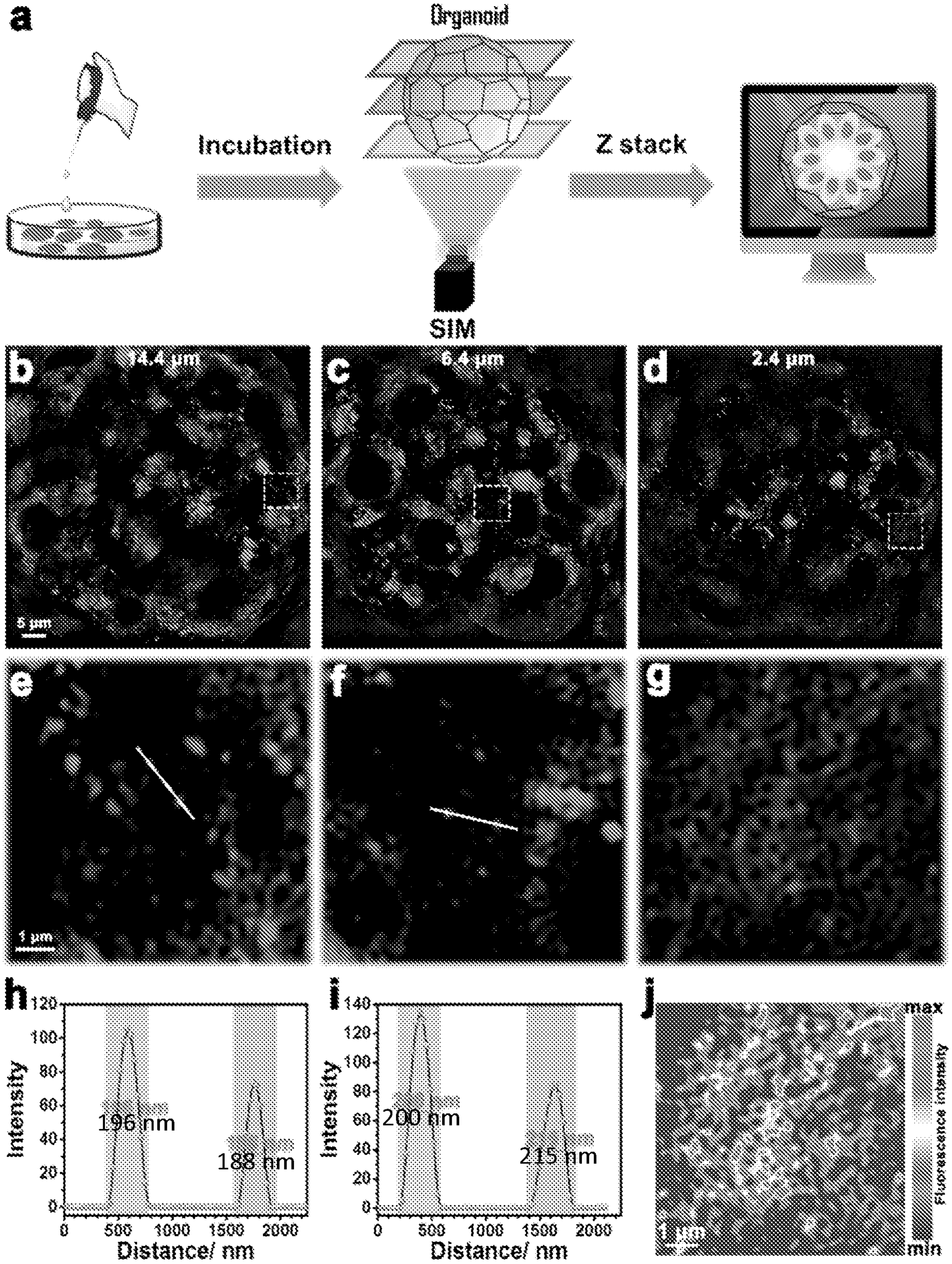
FIG. 7 shows SIM imaging of organoids. (a) is a diagram applied to image organoids using SIM. (b, c, d) show SIM images of organoids at different depths under CCCP treatment. (e, f, g) show local amplification of (b, c, d). (h) and (i) show intensity profiles along the white lines from (e) and (f). (j) shows a fluorescence intensity thermal image of ER morphology from (g) analyzed with ImageJ.

To gauge the spectroscopic sensing behavior of NapBu-BPEA, photophysical properties were tested in a solution of dimethyl suifoxide (DMSO) and 4-(2-hydroxyethyl)-1-piperazineethanesulfonic acid (HEPES) (50 mM, 100 mM $KNO_3$, 1:9, pH 7.2). As shown in FIG. 7, the optical spectra of NapBu-BPEA exhibited a maximum emission peak at 540 nm and maximum absorption peak at 454 nm. The relative fluorescence quantum yield was 0.318, and the molar extinction coefficient was $1.226\times10^4$ $M^{-1}$ $cm^{-1}$. When 1 eq $Zn^{2+}$ was added, the optimum emission peak blue-shifted to 535 nm, with a fluorescence quantum yield of 0.797, and the maximum absorption peak blue-shifted to 445 nm, with a molar extinction coefficient of $1.044\times10^4 M^{-1}$ $cm^{-1}$.

Figure 2:
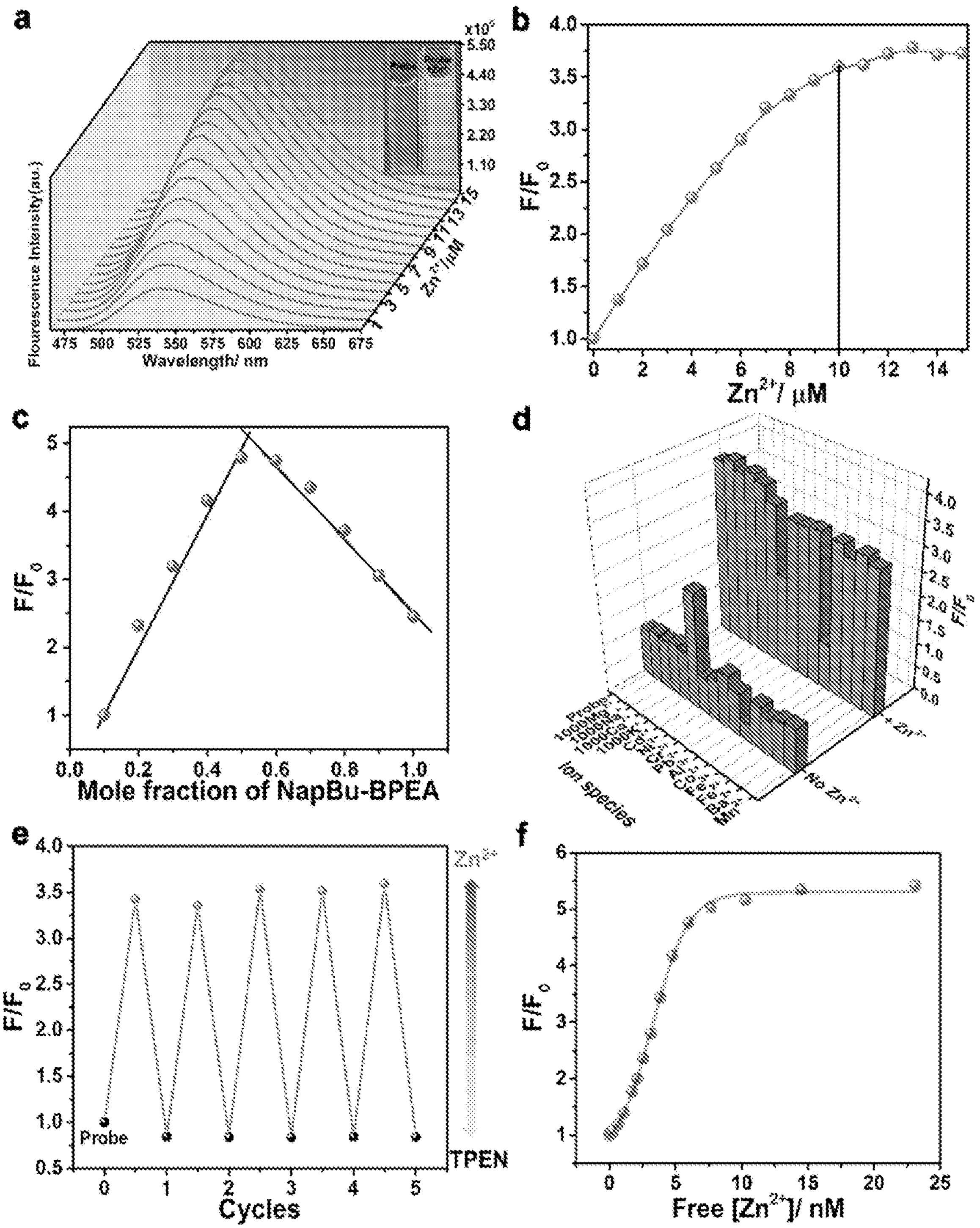
FIG. 2 is series of graphs showing the spectral characterization of NapBu-BPEA. (a) shows the fluorescence titration spectra of NapBu-BPEA (10 μM) with different concentrations of $Zn^{2+}$ in HEPES/DMSO (9:1) and, in the inset, a fluorescence photo of NapBu-BPEA solution before and after the addition of 1 eq $Zn^{2+}$ under 365 nm). (b) shows the $Zn^{2+}$ titration profile of NapBu-BPEA (10 μM) measuring the emission at 540 nm. (c) shows a Job's plot curve of NapBu-BPEA (10 μM) according to emission at 540 nm. (d) shows the fluorescence selectivity and competitive experiment of NapBu-BPEA against metal cation (1,000 eq $K^+$, $Na^+$, $Ca^{2+}$, $Mg^{2+}$; 1 eq $Cd^{2+}$, $Ni^{2+}$, $Cr^{3+}$, $Pb^{2+}$, $Al^{3+}$, $Co^{2+}$, $Fe^{2+}$, $Fe^{3+}$, $Ba^{2+}$, and $Mn^{2+}$). (e) shows the fluorescence reversibility of NapBu-BPEA upon the addition of $Zn^{2+}$ (10 μM) and, in turn, TPEN (10 μM). (f) shows the $Zn^{2+}$ binding constant curve of NapBu-BPEA in HEPES (50 mM, 100 mM $KNO_3$, 10% DMSO, 10 mM EGTA, pH=7.21), $\lambda_{ex}$=450 nm, $\lambda_{ex}$=540 nm.

Next, NapBu-BPEA was titrated with $Zn^{2+}$. As shown in FIG. 2(*a*), owing to the limitations of photoinduced electron transfer (PET), NapBu-BPEA demonstrated an enhanced emission response and an increased concentration of $Zn^{2+}$, which rose by 3.6-fold at 540 nm, accompanied by a slight degree of blue shift. When the concentration of $Zn^{2+}$ totaled 10 μM, the fluorescence intensity achieved saturation (FIG. 2(*a*), (*b*)). UV-vis titration also illustrated a similar phenomenon. As shown by the Job's plot curve in FIG. 2(*c*), the fluorescence intensity peaked when [$Zn^{2+}$]:[NapBu-BPEA] equaled 1:1, which demonstrates that NapBu-BPEA can bind to $Zn^{2+}$ in a 1:1 ratio. The limit of detection was calculated based on the 3 σ/slope method as 54.5 nM. High-resolution mass spectrometry was performed with NapBu-BPEA solution containing 1 eq $Zn^{2+}$, which revealed a peak of 592.1523 belonging to $[NapBu\text{-}BPEA+Zn+Cl]^+$.

Along with detecting $Zn^{2+}$, NapBu-BPEA was tested for interference from other biologically related metal ions, as shown in FIG. 2(*d*). The probe did not respond to any other metal ions except $Cd^{2+}$. When 1 eq $Zn^{2+}$ was added, the fluorescence intensity of NapBu-BPEA clearly increased, whereas it changed only slightly in $Co^{2+}$ and $Ni^{2+}$ solution. However, because the content of $Cd^{2+}$, $Co^{2+}$, and $Ni^{2+}$ in cells was far less than 10 μM, the interference from those metal ions was negligible. These results indicate that NapBu-BPEA has specific fluorescence selectivity for $Zn^{2+}$. Further, following the addition of N,N,N',N'-tetrakis 2-pyridylmethyl ethylenediamine (TPEN), a $Zn^{2+}$-chelating agent, the NapBu-BPEA fluorescence signal enhanced by $Zn^{2+}$ was restored, and an on-off conversion could be observed for five cycles. Taken together, these results indicate that NapBu-BPEA has a favorable reversible response to $Zn^{2+}$ (FIG. 2(*e*)). In an analysis of the function of fluorescence intensity combined with labile $Zn^{2+}$ concentration (FIG. 2(f), the dissociation constant ($K_d$) of the complex between $Zn^{2+}$ and NapBu-BPEA was determined to be 4.98 nM. Last, the effect of pH on the fluorescence response of NapBu-BPEA to $Zn^{2+}$ was investigated by using pH titration. When bound to $Zn^{2+}$, NapBu-BPEA was highly stable at pH 4-8, which indicates that NapBu-BPEA is suitable for detecting $Zn^{2+}$ in a wide range of pH levels.

Example 4

Distribution of NapBu-BPEA in HeLa Cells

Figure 3:
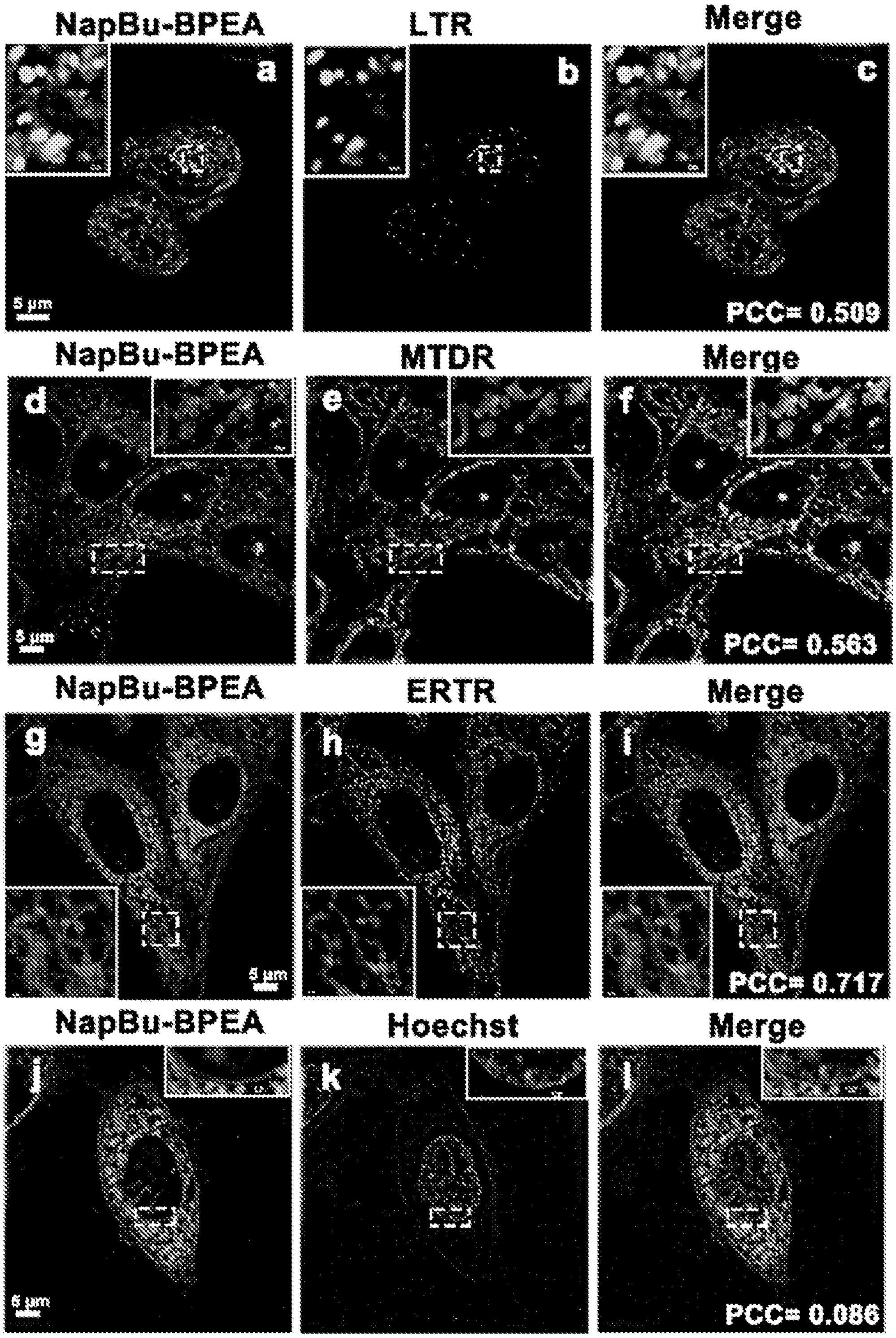
FIG. 3 is a series of SIM images of HeLa cells incubated with NapBu-BPEA and different organelle dyes. (a, b, c) show co-localization images of NapBu-BPEA and lysosome commercial dye (LTR). (d, e, f) show co-localization images of NapBu-BPEA and mitochondrial commercial dye (MTDR). (g, h, i) show co-localization images of NapBu-BPEA and endoplasmic reticulum commercial dye (ERTR). (j, k, l) show co-localization images of NapBu-BPEA and nuclear commercial dye (Hoechst 33258).

Next, the use of NapBu-BPEA to detect fluctuations in intracellular $Zn^{2+}$ was investigated. First, a water-soluble tetrazolium (WST) kit was used to determine the cytotoxic activity of NapBu-BPEA by measuring the activity of lactate dehydrogenase released into the medium. After incubating HeLa cells with different concentrations of NapBu-BPEA for 24 h, it was observed that when the concentration reached 20 μM, the activity of the lactate dehydrogenase was less than 20%, while the cell viability exceeded 80%. Together, this data indicates that NapBu-BPEA has a low cytotoxicity and is highly suitable for cell imaging. To ascertain the incubation time, SIM images of HeLa cells were co-incubated with NapBu-BPEA at various time points, which revealed that the fluorescence signal of NapBu-BPEA entering the cells changed only slightly after 1 h of incubation. These results suggest that 1 h is the optimal incubation time for cell imaging. To evaluate the staining ability of NapBu-BPEA, the commercially available lysosomal dye LysoTracker Red (LTR), the commercial mitochondrial dye MitoTracker Deep Red (MTDR), the endoplasmic reticulum dye ER-Tracker Red (ERTR), and the nuclear dye Hoechst 33258 (Hoechst) were used in a co-localization experiment. Therein, HeLa cells were incubated with NapBu-BPEA and commercial dyes at 37° C. As shown in FIG. 3, a strong green fluorescence signal was observed in the green channel, which was attributed to NapBu-BPEA, whereas the other channels (i.e., blue, red, and magenta) showed fluorescence signals of punctate lysosomes, rod mitochondria, reticular endoplasmic reticulum, and round nuclei. By calculating the co-localization Pearson's coefficient and the magnification of the overlapping images, it was found that NapBu-BPEA had distributed within all organelles except the nucleus. Together, the results indicate that NapBu-BPEA can be used to monitor the level of $Zn^{2+}$ in individual organelles throughout entire cells.

Example 5

Super-Resolution Imaging of Change in $Zn^{2+}$ Level

Figure 4:
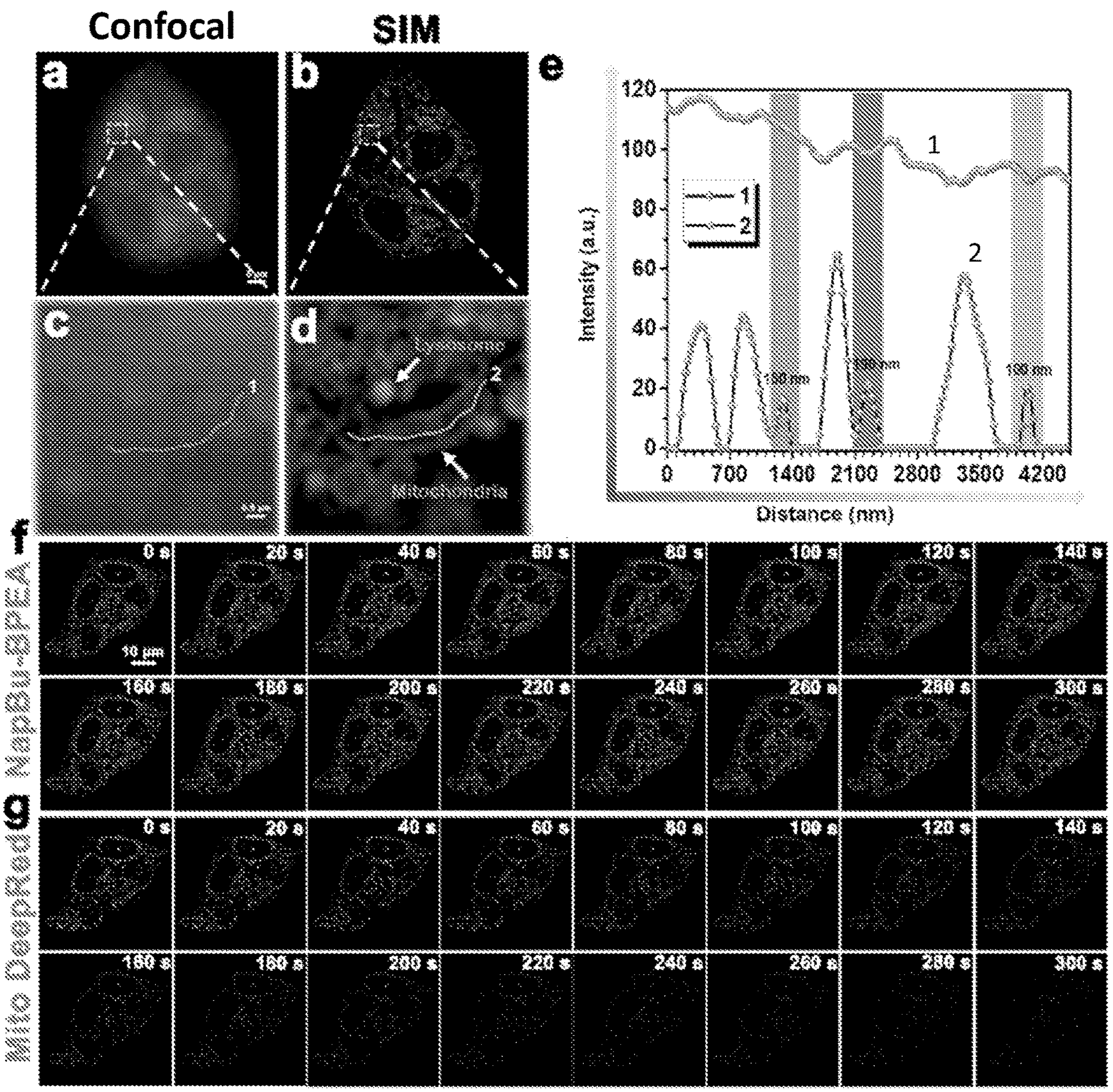
FIG. 4 is a series of confocal and super-resolution images and photobleaching of NapBu-BPEA in HeLa cells. (a) shows a confocal image. (b) shows a SIM image. (c) shows a local magnification from (a). (d) shows local magnification from (b). (e) shows a blue-dotted line indicating fluorescence intensity along the line in (c) and a red-dotted line indicating fluorescence intensity along the line in (d). (f) shows SIM images illuminated by NapBu-BPEA at different times. (g) shows SIM images illuminated by MTDR at different times.

The visualization of organelle ultrastructures can illuminate the pathology and diagnosis of intracellular diseases. To study the ultrastructural information of intracellular organelles, NapBu-BPEA was used to perform the ultrastructural imaging of organelles in living cells under 3D-SIM. As shown in FIG. 4(*a*)-(*d*), confocal and SIM imaging of HeLa cells after 1 h of incubation revealed that NapBu-BPEA afforded a good super-resolution display of lysosomes, represented by dots, and mitochondria, represented by rods with cristae. Next, the mitochondrial intensity of the confocal and SIM images was analyzed, which supported NapBu-BPEA's ability to clearly distinguish the structure of mitochondrial cristae under SIM. To further clarify the resolution of NapBu-BPEA, a full width and half peak (FWHM) up to 100 nm under SIM was obtained (FIG. 4(*e*)), which overcame the optical diffraction limit and achieved super-resolution imaging. These results indicate that NapBu-BPEA can provide excellent accuracy and resolution under SIM.

At the same time, because NapBu-BPEA's optical stability is an important factor in super-resolution imaging, a long-term continuous laser (300 s) stimulation of cells was carried out, capturing images every 20 s in order to monitor the photostability of NapBu-BPEA and MTDR in cells (FIG. 4(*f*), (*g*)). Among the results, NapBu-BPEA had stained cells and showed negligible photobleaching within 300 s of laser stimulation, while after 120 s, MTDR's fluorescence intensity had decreased to less than 30%. These characteristics enabled NapBu-BPEA to dynamically monitor cellular ultrastructures with long-term super-resolution imaging.

In view of these promising results, a 1:2 mixture of $ZnCl_2$ and pyrithione sodium salt, a cell-permeable $Zn^{2+}$ carrier (ZnPT) to transport exogenous $Zn^{2+}$ to cells, and a cell-permeable $Zn^{2+}$-chelating agent, TPEN, were used to evaluate the reversibility of fluorescence response to $Zn^{2+}$ in living cells according to methods described elsewhere. To determine the entry time of exogenous $Zn^{2+}$ into cells, NapBu-BPEA was incubated and an initial image was captured, after which 50 μM ZnPT (50 μM $ZnCl_2$/100 μM pyrithione sodium salt) was used to replace the culture medium in dye-free and serum-free DMEM. Images collected in situ every 2 min ultimately showed that the fluorescence intensity was balanced after exogenous $Zn^{2+}$ was incubated with HeLa cells for 6 min. Moreover, when NapBu-BPEA was added by exogenous $Zn^{2+}$, it continued to exhibit fluorescence in the cytoplasm, which differed from when Naph-BPEA fluoresced in the nucleus upon being added to exogenous $Zn^{2+}$. The variance may be attributed to the difference in lipophilicity. Before the addition of exogenous $Zn^{2+}$, NapBu-BPEA showed an exceptionally weak fluorescence background signal in HeLa cells. When different concentrations of exogenous $Zn^{2+}$ were added, however, the fluorescence signal increased significantly and intensified with the increased concentration of ZnPT. These results indicate that NapBu-BPEA can be used in imaging intracellular $Zn^{2+}$ in living cells.

To test whether NapBu-BPEA responds reversibly to $Zn^{2+}$ in cells, TPEN was used to chelate $Zn^{2+}$ in cells. When 100 μM TPEN was added to the cells, the fluorescence signal of NapBu-BPEA-labeled cells attenuated significantly, which indicates that NapBu-BPEA can respond reversibly to intracellular $Zn^{2+}$.

Example 6

Monitoring Endogenous $Zn^{2+}$ During Autophagy in HeLa ells

Mitophagy, a type of autophagy, is necessary for cells to maintain homeostasis. To study the relationship between autophagy and $Zn^{2+}$, carbonyl cyanide m-chlorophenylhydrazone (CCCP), a mitochondrial damage inducer, was used to induce mitophagy in HeLa cells. When the cells were treated with CCCP and incubated with NapBu-BPEA, the overall fluorescence signal of the CCCP-treated cells improved significantly compared with the signal of untreated cells, and bright spots appearing in the cytoplasm were highly coincident with DAPRed, an autophagy detection reagent. Further, subsequent treatment with TPEN prompted the recovery of enhanced fluorescence signals, which indicates that the enhanced signals during cell damage derived from an increased level of $Zn^{2+}$.

Considering that ATG13 and FIP200 are essential proteins for autophagy, to further elucidate the relationship between autophagy and changes in level of $Zn^{2+}$ two stable knockout (KO) cell lines were obtained (ATG13 KO HeLa cells and FIP200 KO HeLa cells) via CRISPR/Cas9 gene editing technology. Lacking the proteins necessary for autophagy, these KO cells do not undergo autophagy. Once the two cell lines were treated with CCCP, no significant change in fluorescence intensity occurred between the treated and untreated KO cells. Such outcomes confirmed that when mitophagy occurs, the level of $Zn^{2+}$ in cells increases, and when autophagy is blocked, the level of $Zn^{2+}$ does not change significantly.

Figure 5:
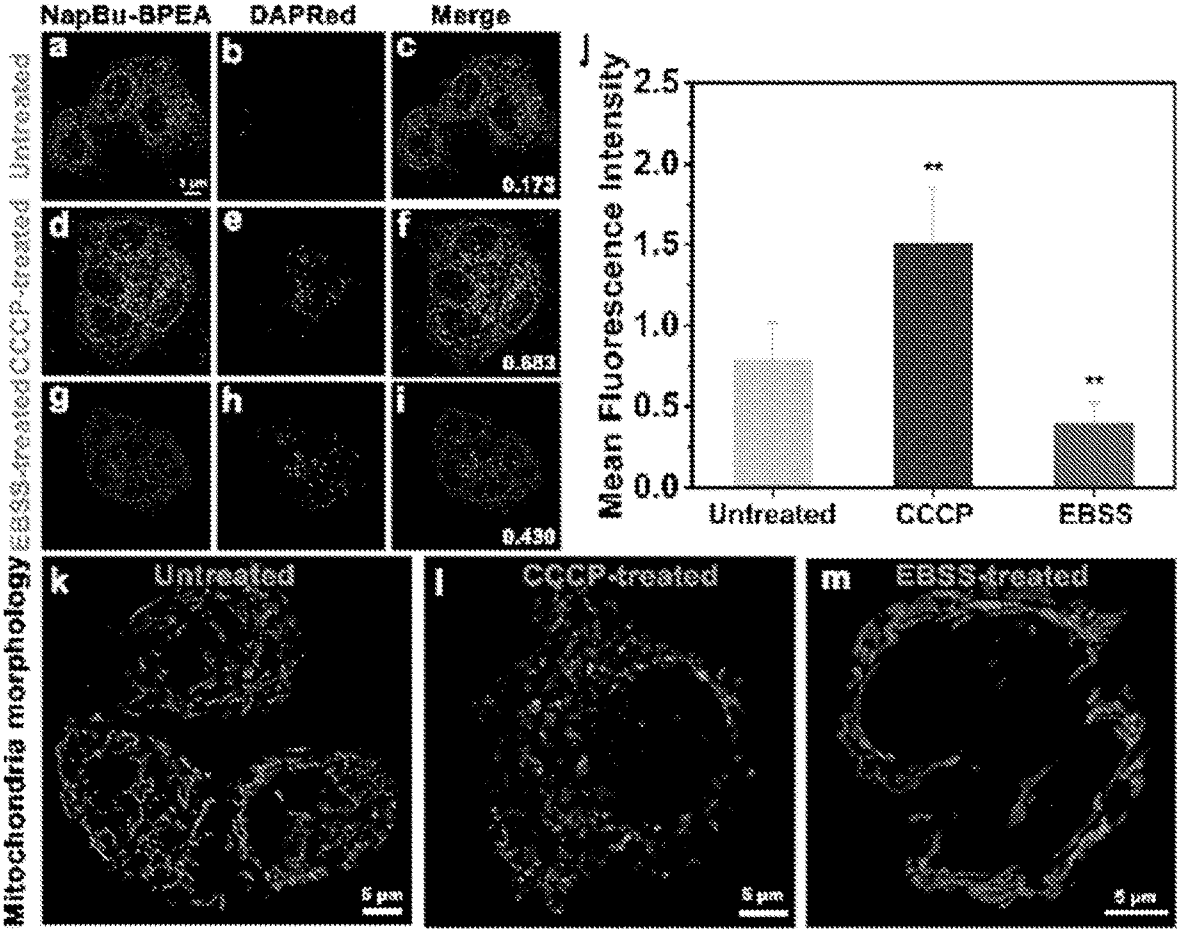
FIG. 5 is a series of SIM images of HeLa cells incubated with NapBu-BPEA (10 μM) and DAPRed without treatment, with CCCP treatment, and with EBSS treatment, along with SIM images of HeLa cells stained with mitochondrial commercial dye (i.e., MTG). (a, d, g) show the green channel from NapBu-BPEA-incubated HeLa cells. (b, e, h) show the red channel from DAPRed-incubated HeLa cells. (c, f, i) show overlapping images of red and green channels. (j) shows the quantification of fluorescence intensity from (a, d, g). (k, l, m) show mitochondrial morphology under different treatments. Average fluorescence intensity readouts of green channel (n=6 per group, Mean+SD, *p<0.01, **p<0.05).

Autophagy is generally divided into two types: selective autophagy (i.e., CCCP-induced mitophagy) and non-selective autophagy (i.e., Earle's Balanced Salt Solution (EBSS)-induced autophagy). Mitochondrial morphology in cells stained with commercial mitochondrial dye (MTG) changed from rod-shaped (FIG. 5(*k*)) to dot-shaped (FIG. 5(*l*)) after treatment with CCCP. Although autophagy occurred when HeLa cells were starved with EBSS for 24 h, after staining mitochondria with MTG, it was found that the mitochondrial morphology remained stick-shaped, which complicated judging whether starvation autophagy occurred by staining with MTG. Surprisingly, when autophagy was induced by CCCP and EBSS, respectively, and stained with NapBu-BPEA, the fluorescence signal of cells treated with CCCP improved significantly, whereas the fluorescence intensity of cells treated with EBSS decreased (FIG. 5). These results indicate that changes in level of $Zn^{2+}$ differ in cells subjected to different treatments. The process of autophagy is highly complex and involves a great deal of Zn-related proteins; therefore, the observed upregulation or downregulation of $Zn^{2+}$ level may have occurred by way of a more complex, indirect mechanism. While not desiring to be bound by theory, these data show that NapBu-BPEA can detect and distinguish changes in $Zn^{2+}$ level under different types of autophagy.

Example 7

Super-Resolution Morphology-Correlated Detection of $Zn^{2+}$

Figure 6:
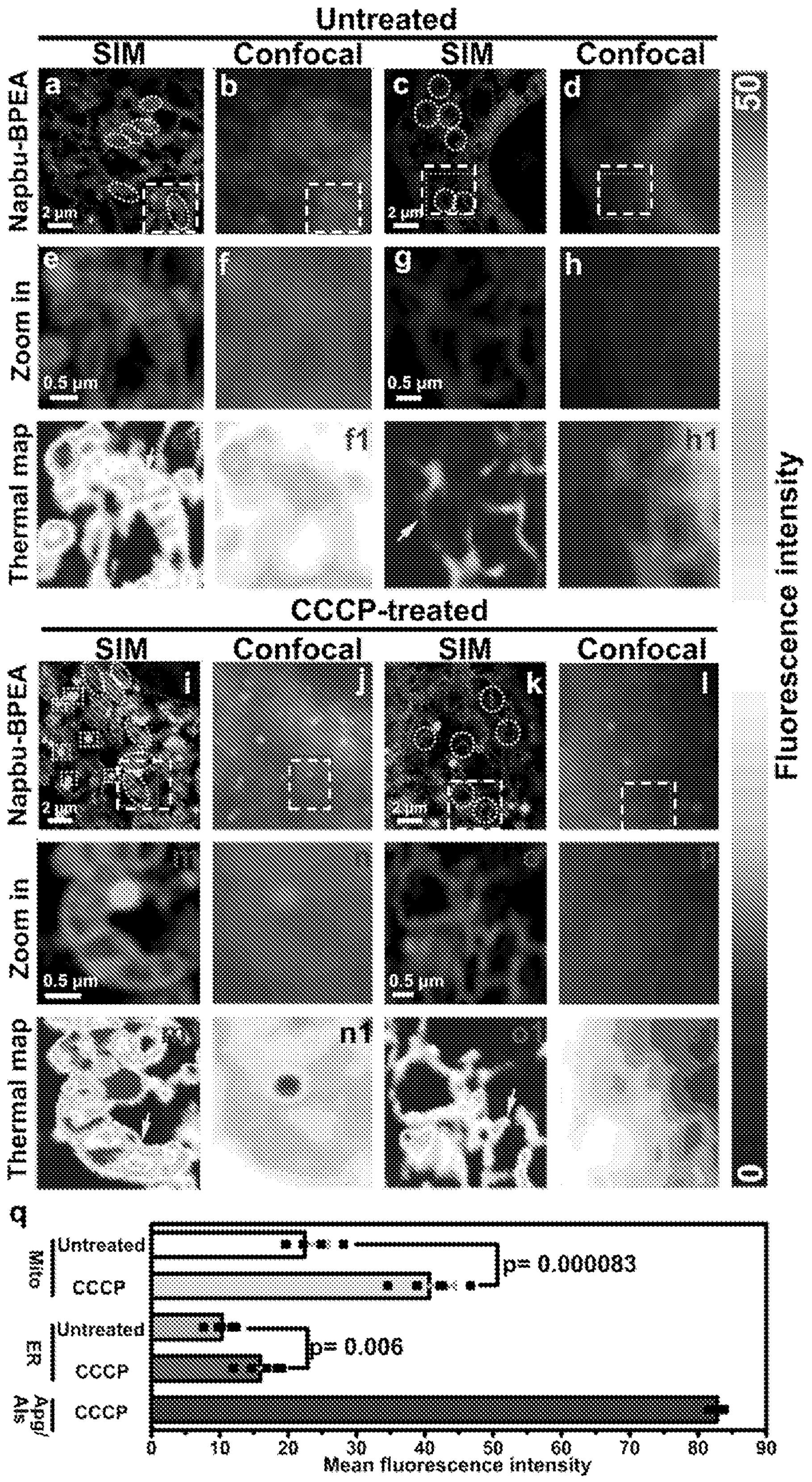
FIG. 6 shows subcellular $Zn^{2+}$ level changes under different conditions in super-resolution imaging and confocal imaging. (a, c, i, k) show SIM images of NapBu-BPEA-loaded HeLa cells without treatment or with CCCP treatment. (b, d, j, l) show confocal images of NapBu-BPEA-loaded HeLa cells without treatment or with CCCP treatment. (e-h), (m-p) show enlarged images on frames from (a-d), (i-l). (el-hl), (ml-pl) show show fluorescence intensity thermal images constructed from (e-h), (m-p), respectively. (q) shows mean fluorescence intensity for mitochondria, endoplasmic reticulum, autophagosome/autolysosome. Scale bar: 2 μm, enlarged images scale bar: 0.5 μm.

Despite the clear relationship between autophagy and the level of $Zn^{2+}$ in entire cells, effective methods of detecting changes in levels of $Zn^{2+}$ in various organelles during autophagy remain a challenge. Because NapBu-BPEA is distributed throughout all cytosolic organelles, using super-resolution imaging technology combined with SIM allows distinguishing individual organelles by morphological features (FIGS. 3 and 4). Super-resolution MCoD methods can be used to further observe changes in levels of $Zn^{2+}$ in organelles during autophagy. As shown in FIG. 6, the different treatments of HeLa cells were first analyzed via SIM imaging and confocal imaging, to obtain a thermal map of the $Zn^{2+}$ level via fluorescence intensity analysis. Despite the difficulty of differentiating organelles in blurred confocal images, it is easy to distinguish organelles according to their different morphologies in high-resolution SIM images, as evidenced in the mitochondria in FIGS. 6(*e*1) and (*m*1), the endoplasmic reticulum in FIGS. 6(*g*1) and (*o*1), and autophagosomes in bright spots. These data demonstrate that NapBu-BPEA can be applied in super-resolution imaging to differentiate organelles without the need for co-localization with commercial dyes.

Further, as the thermal map distribution revealed, the distribution of fluorescence intensity in each organelle was heterogeneous. The fluorescence intensity on the mitochondrial cristae exceeded that of the mitochondrial matrix, and the distribution of the fluorescence intensity of the endoplasmic reticulum was uneven. Together, these results indicate that super-resolution imaging allows the observation of the distribution of $Zn^{2+}$ in each organelle. By extension, to investigate changes in levels of $Zn^{2+}$ in organelles during autophagy, mitochondria or endoplasmic reticula were randomly selected as regions of interest via morphology, as shown in FIGS. 6(*a*), (*c*), (*i*,) and (*k*), respectively. Shown in FIG. 6(*q*), the analysis of fluorescence intensity revealed that the level of $Zn^{2+}$ in mitochondria had increased by 1.89-fold during autophagy, whereas that of endoplasmic reticulum had increased by 1.55-fold. While not desiring to be bound by theory, these results suggest that the level of $Zn^{2+}$ in mitochondria changes more than that in ER during autophagy, possibly because CCCP can change the mitochondrial membrane potential. The results confirmed that super-resolution MCoD is useful for monitoring labile $Zn^{2+}$ at the subcellular level.

Example 8

SIM Imaging of Organoids

The detection of $Zn^{2+}$ at the cellular level offers limited information regarding organelles and tissues. As better in vitro culture systems, organoids can mimic certain key characteristics of organs. With a structure and function similar to those of organs, organoids are self-assembled structures, usually formed by the differentiation of stem cells cultured in vitro. Because organoids can readily mimic the structure and function of real organs compared with in vitro cell models, they afford not only significant advantages in scientific research and drug development, but also provide convenience for the simulation of human organs. For the 3D super-resolution imaging of organoids with SIM, the major obstacle is the presence of too much out-of-focus light, which prevents imaging the grating sufficiently to receive useful information. To reduce fluorescent background from high-excitation laser power, probes with high quantum yields may be useful.

Accordingly, NapBu-BPEA was used to image organoids with methods depicted in FIG. 7(*a*). Organoids treated with CCCP for 24 h were incubated with NapBu-BPEA for 2 h and subjected to SIM imaging at different depths. As shown in FIG. 7(*b*)-(*d*), NapBu-BPEA is successfully imaged at different depths and is functional to distinguish organically combined pluripotent stem cells. Even for the imaging of organoids, SIM provides a resolution below 200 nm (FIG. 7(*e*), (*f*), (*h*), (*i*)), which indicates that NapBu-BPEA can be employed for super-resolution imaging, which is a useful method of studying and visualizing species in organoids. Moreover, as shown in FIGS. 7(*g*) and (*j*), from the local image of a certain section of an organoid, the endoplasmic reticulum is clearly identified by its morphological features. These results indicate that MCoD can be applied to image organoids as well as cells.

Example 9

NapBu-BPEA Can Sense Intracellular Labile $Zn^{2+}$ in a Reversible Manner

Next, NapBu-BPEA was investigated for its intracellular labile $Zn^{2+}$ imaging ability. Imaging experiments were performed in HeLa cells upon exogenous $Zn^{2+}$ loading via incubation with zinc pyrithione cmplex (ZnPT), a cell-permeable $Zn^{2+}$ carrier.

Intracellular labile $Zn^{2+}$ enhancement processes were tracked by recording SIM images every 2 min. The imaging revealed an instant fluorescence enhancement upon ZnPT (50 μM) incubation, displaying an almost linear increase in the first 4 min (FIG. 8(*a, b*)). The stable fluorescence signal after 4 min indicated that the exogenous $Zn^{2+}$ loading process is completed quickly. During the $Zn^{2+}$ loading process, in addition to the intensity enhancement, the punctate fluorescence in the cytoplasm was retained and no fluorescence appeared in the nucleus even after 1 h of ZnPT incubation. This intracellular distribution behavior was clearly different from the redistribution behavior of NaphBPEA upon $Zn^{2+}$ loading, which resulted in the uniform fluorescence in the cytoplasm and nucleus. While not desiring to be bound by theory, it is proposed that the butyl tail of NapBu-BPEA is responsible for the retained multiple organelle accumulation behavior of NapBu-BPEA upon $Zn^{2+}$ binding.

Figure 8:
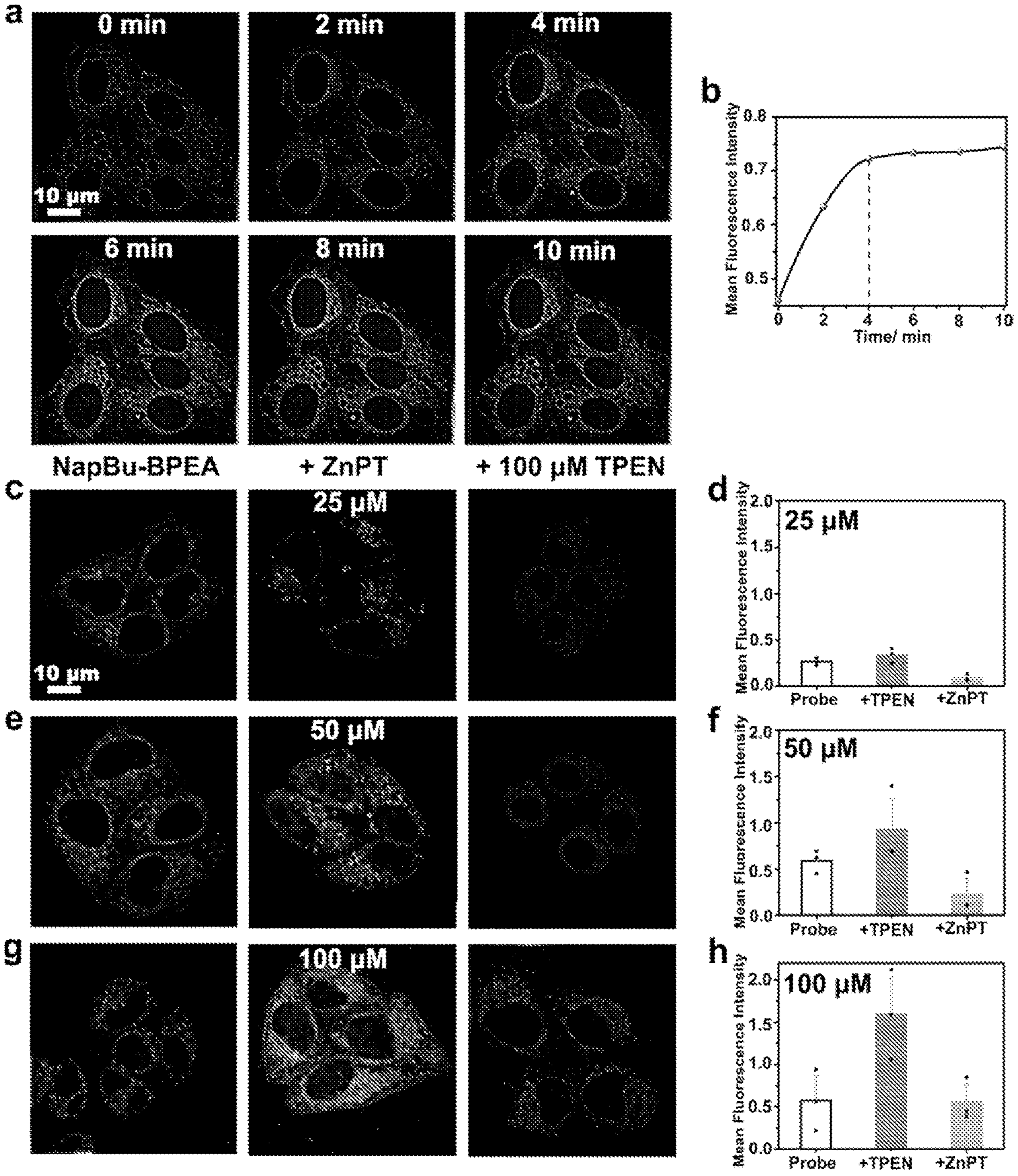
FIG. 8 shows NapBu-BPEA senses $Zn^{2+}$ in a reversible manner. (a) shows SIM imaging of the NapBu-BPEA-stained HeLa cells (10 μM, 1 h, 37° C.) upon incubation with 50 μM ZnPT. (b) shows the corresponding temporal profile of intracellular fluorescence increase. (c-h) relate to SIM imaging of the probe-stained (10 μM, 1 h, 37° C.) HeLa cells undergoing ZnPT (25 μM, (c, d); 50 μM, (e, 0; 100 μM, (g, h)) incubation (10 min) and subsequent TPEN (100 μM, 30 min) treatment; and the corresponding histograms (d, f, h) of the determined average fluorescence intensity in cells from n=3 biologically independent experiments, mean+SD. Scale bar, 10 μm.
Figure 9:
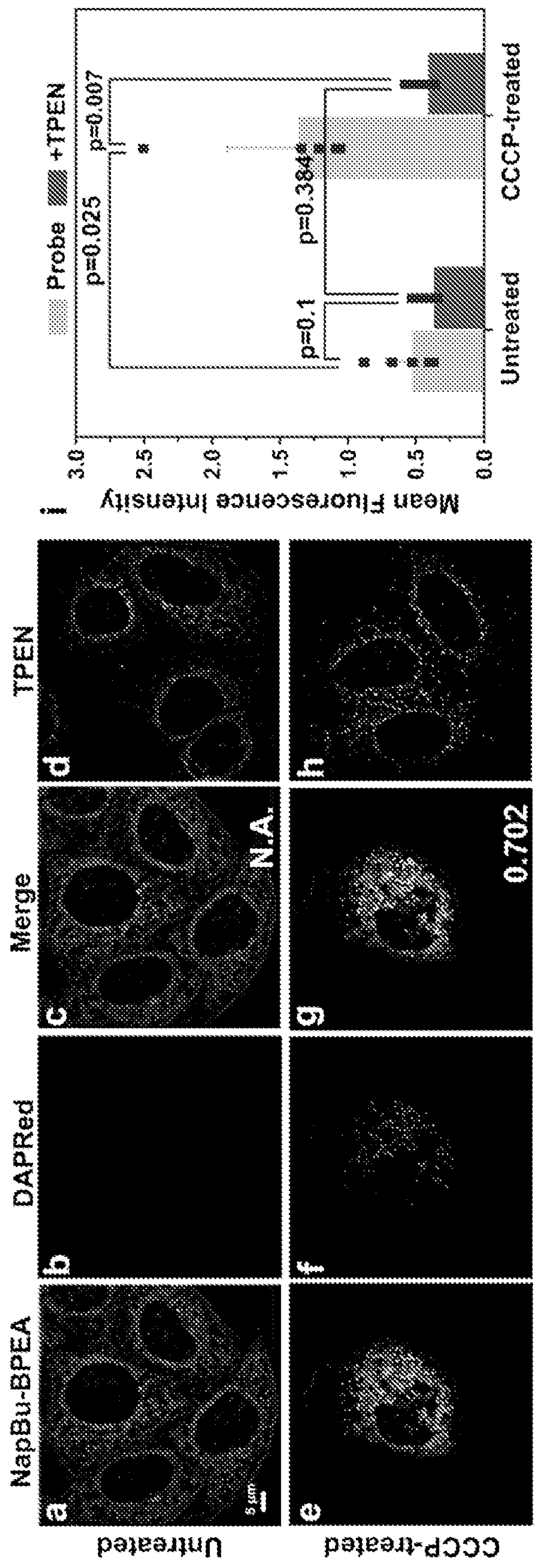
FIG. 9 shows NapBu-BPEA reveals labile $Zn^{2+}$ dynamics in autophagic HeLa cells. SIM images of HeLa cells stained by NapBu-BPEA and DAPRed without (a-d) or with (e-h) CCCP (10 μM, 24 h, 37° C.) treatment are shown. (a, e) show cell images from the green channel for NapBu-BPEA (10 μM, 1 h, 37° C.) fluorescence. (b, f) show cell images from the red channel for DAPRed (1 μM, 30 min, 37° C.) fluorescence. (c, g) show merged images of red and green channel images. (d, h) cell images for cells in (a, b) underwent TPEN (100 μM, 30 min, 37° C.) treatment. (i) shows the average fluorescence intensity recorded in the green channel images for cells with or without CCCP treatment. n=6 biologically independent experiments per group, mean+SD, the statistical differences between the experimental groups were analyzed by double-tailed Student's t test, when p<0.05, it was considered to have statistical significance. Scale bar, 5 μm.

Higher ZnPT concentration led to higher fluorescence enhancement in the cytoplasm (FIG. 8 (*c-h*)), implying that NapBu-BPEA enables fluorescence tracking of labile $Zn^{2+}$ enhancement in cells. Intracellular $Zn^{2+}$ scavenging for the $Zn^{2+}$-loaded HeLa cells with TPEN (a cell membrane permeable $Zn^{2+}$ scavenger) treatment resulted in a distinct drop in cytoplasmic fluorescence. This confirmed that the fluorescence enhancement upon ZnPT incubation was really associated with labile $Zn^{2+}$ enhancement, and NapBu-BPEA was able to sense intracellular labile $Zn^{2+}$ in a reversible manner. The punctate fluorescence distribution pattern was still retained in this $Zn^{2+}$ scavenging process.

Example 10

NapBu-BPEA Reveals Labile $Zn^{2+}$ Dynamics in Autophagic HeLa Cells

Figure 10:
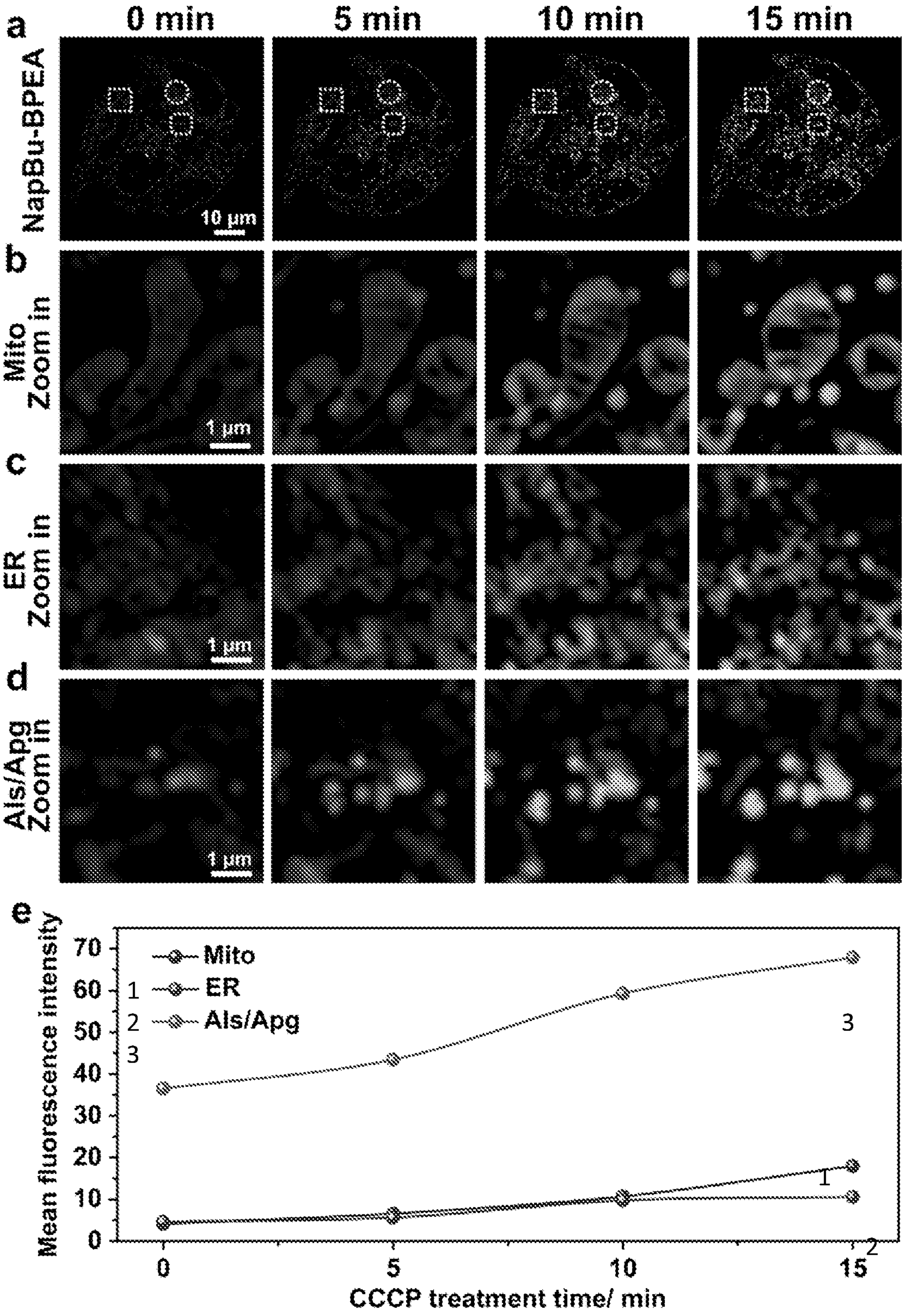
FIG. 10 shows NapBu-BPEA tracking of labile $Zn^{2+}$ in mitophagy. (a) shows time-lapse SIM images of HeLa cells stained by NapBu-BPEA recorded upon incubation with 20 μM CCCP; and zoom-in images of regions of interest marked with squares (b, mitochondria), circles (c, ERs), and rounded squares (d, autophagosomes/autolysosomes). (e) shows temporal profiles of mean fluorescence intensity detected for mitochondria, ERs, and autophagosomes/autolysosomes in HeLa cells shown in (a-d).

With the reversible $Zn^{2+}$ imaging ability and the multiple organelle distribution behavior upon $Zn^{2+}$ binding, NapBu-BPEA was investigated for its application in simultaneous $Zn^{2+}$ tracking in multiple organelles (Zn-STIMO) for autophagic cells. HeLa cells were incubated with carbonyl cyanide m-chlorophenylhydrazone (CCCP, a mitochondrial damage inducer) as a mitophagy model. The cells were co-stained with NapBu-BPEA and DAPRed, an autophagy dye incorporating into the autophagosome during double-membrane formation via structural features and emitting under hydrophobic conditions. As shown in FIG. 10, SIM imaging in the DAPRed channel for HeLa cells without CCCP incubation showed no red fluorescence, while the red fluorescence in the cells with 24 h of CCCP exposure (10 μM) confirmed the mitophagy induction. SIM imaging in the NapBu-BPEA channel showed that the green fluorescence intensity of NapBu-BPEA in the mitophagic cells was ~2.0-fold higher than that in non-autophagic cells (FIG. 10(*i*)). Subsequent TPEN treatment decreased the fluorescence to a level slightly lower than that of cells without autophagy. This reversible fluorescence response in the green channel indicated that the detected NapBu-BPEA fluorescence change was caused by labile $Zn^{2+}$ fluctuation, and that NapBu-BPEA was able to visualize labile $Zn^{2+}$ fluctuation in mitophagy. In addition, the dynamic labile $Zn^{2+}$ tracking in cells exposure to CCCP (20 μM) disclosed that the autophagy induction processes underwent rapid enhancement of labile $Zn^{2+}$ in the initial 5 min of CCCP incubation, followed by and the subsequent slower $Zn^{2+}$ enhancement (data not shown), and the temporal profile of the reversible labile $Zn^{2+}$ decrease induced by TPEN treatment 14 mins post CCCP incubation was also observed.

Example 11

NapBu-BPEA Imaging Can Monitor $Zn^{2+}$ in Different Organelles Simultaneously

The $Zn^{2+}$ level in cells changes from time to time, so tracking dynamic $Zn^{2+}$ in living cells is an important goal. Here, dynamic labile $Zn^{2+}$ tracking was performed in the CCCP-induced mitophagy of HeLa cells via Zn-STIMO (FIG. 10). The temporal profiles of mean fluorescence in the mitochondria, ER, and autophagosome/autolysosome (Aps/Als) revealed that the distinct labile $Zn^{2+}$ enhancement appeared 5 min later than CCCP incubation, and the Aps/Als displayed the more distinct enhancement of labile $Zn^{2+}$ than the mitochondria and ERs (FIG. 10(*e*)). This dynamic tracking of labile $Zn^{2+}$ demonstrated the capability of Zn-STIMO via SIM imaging to detect labile $Zn^{2+}$ fluctuation in different organelles.

Embodiments can be described with reference to the following numbered clauses, with preferred features laid out in dependent clauses.

1. A method for detecting labile zinc ($Zn^{2+}$) in a biological material, the method comprising:
   (a) contacting the biological material with a composition comprising NapBu-BPEA, having the structure

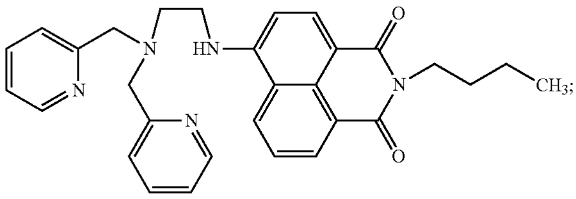 [SMILES: CCCCN1C(=O)c2cccc3c(NCCN(Cc4ccccn4)Cc4ccccn4)ccc(c23)C1=O]

and (b) imaging the biological material via molecular fluorescence imaging to detect the labile zinc in the biological material.
2. The method according to clause 1, wherein the molecular fluorescence imaging comprises super-resolution imaging.
3. The method according to clause 2, wherein the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM).
4. The method according to any of clauses 2-3, wherein the super-resolution imaging is SIM and has a spatial resolution peak of about 100 nm.
5. The method according to any of the preceding clauses, wherein the biological material comprises an organoid or a living cell.
6. The method according to any of the preceding clauses, wherein the biological material is in situ or in vivo.
7. The method according to any of the preceding clauses, wherein detecting the labile zinc comprises visualizing a distribution of labile zinc in the biological material.
8. The method according to any of the preceding clauses, further comprising correlating the distribution of labile zinc in the biological material with a morphological feature of a subcellular organelle to determine labile zinc localization in the subcellular organelle.
9. The method according to clause 8, wherein the morphological feature of the subcellular organelle is selected from the group consisting of shape, structure, size, and combinations thereof.
10. The method according to any of the preceding clauses, wherein the NapBu-BPEA does not comprise a specific subcellular organelle-targeting group.
11. The method according to any of the preceding clauses, wherein the method does not comprise co-localization with a second dye.
12. The method according to any of the preceding clauses, wherein the NapBu-BPEA binds $Zn^{2+}$ in a 1:1 ratio.
13. The method according to any of the preceding clauses, wherein the NapBu-BPEA binds $Zn^{2+}$ reversibly.
14. The method according to any of the preceding clauses, further comprising quantifying the labile zinc in the biological material based on the imaging of step (b).
15. A method for morphology-correlated detection of labile zinc ($Zn^{2+}$) localization in a subcellular organelle of a living cell, the method comprising:
   (a) contacting the cell with a composition comprising NapBu-BPEA;
   (b) imaging the cell via super-resolution imaging to visualize a distribution of labile zinc in the cell; and
   (c) correlating the distribution of labile zinc in the cell with at least one morphological feature of the subcellular organelle to determine labile zinc localization in the subcellular organelle.
16. The method according to clause 15, further comprising:
   (d) repeating steps (b) and (c) at determined time intervals and comparing obtained super-resolution imaging data obtained at the determined time intervals to track a change in labile zinc localization in the subcellular organelle over time.
17. The method according to any of clauses 15-16, wherein the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM).
18. The method according to any of clauses 15-17, wherein the super-resolution imaging is SIM and has a spatial resolution peak of about 100 nm.
19. The method according to any of clauses 15-18, wherein the living cell is in situ or in vivo.
20. The method according to any of clauses 15-19, wherein the morphological feature of the subcellular organelle is selected from the group consisting of shape, structure, size, and combinations thereof.
21. The method according to any of clauses 15-20, wherein the NapBu-BPEA does not comprise a specific subcellular organelle-targeting group and wherein the method does not comprise co-localization with a second dye.
22. A method of tracking a change in labile zinc ($Zn^{2}$) localization in a biological material, the method comprising:
   (a) contacting the biological material with a composition comprising NapBu-BPEA;
   (b) imaging the biological material via super-resolution imaging to detect the labile zinc in the biological material;
   (c) repeating step (b) at determined time intervals and comparing obtained super-resolution imaging data to track the change in labile zinc localization in the biological material over time.
23. The method according to clause 22, wherein the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM).

24. The method according to any of clauses 22-23, wherein the super-resolution imaging is SIM and has a spatial resolution peak of about 100 nm.

25. The method according to any of clauses 22-24, wherein the biological material is a cell or an organoid.

26. The method according to any of clauses 22-25, wherein the NapBu-BPEA does not comprise a specific subcellular organelle-targeting group.

27. The method according to any of the preceding clauses, wherein imaging data obtained from molecular fluorescence imaging, super-resolution imaging, and/or SIM imaging is correlated with morphological features of subcellular organelles selected from the group consisting of mitochondrial rod shapes, mitochondrial cristae, punctate lysosomes, and reticular endoplasmic reticulum to detect, visualize, or track labile zinc localization in subcellular organelles.

All documents cited are incorporated herein by reference in their entirety; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

The foregoing description is illustrative of particular embodiments of the invention but is not meant to be a limitation upon the practice thereof. While particular embodiments have been illustrated and described, it would be obvious to one skilled in the art that various other changes and modifications can be made without departing from the spirit and scope of the invention. It is therefore intended to cover in the appended claims all such changes and modifications that are within the scope of this invention.

The invention claimed is:

1. A method for detecting labile zinc ($Zn^{2+}$) in a biological material, the method comprising:

(a) contacting the biological material with a composition comprising 2,4-(bis(pyridin-2-ylmethyl) aminoethyl) amino-N-n-butyl-1,8-naphthalimide (NapBu-BPEA), having the structure

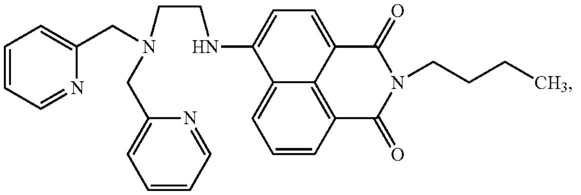 [SMILES: CCCCN1C(=O)c2cccc3c(NCCN(Cc4ccccn4)Cc4ccccn4)ccc(c23)C1=O]

wherein the NapBu-BPEA binds to the labile zinc and fluoresces upon excitation; and (b) imaging the biological material via molecular fluorescence imaging to detect the labile zinc in the biological material.

2. The method according to claim 1, wherein the molecular fluorescence imaging comprises super-resolution imaging.

3. The method according to claim 2, wherein the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM).

4. The method according to claim 3, wherein imaging data obtained from the super-resolution imaging is correlated with morphological features of subcellular organelles selected from the group consisting of mitochondrial rod shapes, mitochondrial cristae, punctate lysosomes, and reticular endoplasmic reticulum to detect, visualize, or track labile zinc localization in subcellular organelles.

5. The method according to claim 2, wherein the super-resolution imaging is structured illumination microscopy (SIM) and has a spatial resolution peak of about 100 nm.

6. The method according to claim 1, wherein the biological material comprises an organoid or a living cell.

7. The method according to claim 6, wherein the biological material is in situ or in vivo.

8. The method according to claim 1, wherein detecting the labile zinc comprises visualizing a distribution of labile zinc in the biological material.

9. The method according to claim 8, further comprising correlating the distribution of labile zinc in the biological material with a morphological feature of a subcellular organelle to determine labile zinc localization in the subcellular organelle.

10. The method according to claim 9, wherein the morphological feature of the subcellular organelle is selected from the group consisting of shape, structure, size, and combinations thereof.

11. The method according to claim 9, wherein the NapBu-BPEA does not comprise a specific subcellular organelle-targeting group.

12. The method according to claim 9, wherein the method does not comprise co-localization with a second dye.

13. The method according to claim 1, wherein the NapBu-BPEA binds $Zn^{2+}$ in a 1:1 ratio.

14. The method according to claim 1, wherein the NapBu-BPEA binds $Zn^{2+}$ reversibly.

15. The method according to claim 1, further comprising quantifying the labile zinc in the biological material based on the imaging of step (b).

16. A method for morphology-correlated detection of labile zinc ($Zn^{2+}$) localization in a subcellular organelle of a living cell, the method comprising:

(a) contacting the cell with a composition comprising 2,4-(bis(pyridin-2-ylmethyl) aminoethyl) amino-N-n-butyl-1,8-naphthalimide (NapBu-BPEA), wherein the NapBu-BPEA binds the labile zinc and fluoresces upon excitation;

(b) imaging the cell via super-resolution imaging to visualize a distribution of labile zinc in the cell; and (c) correlating the distribution of labile zinc in the cell with at least one morphological feature of the subcellular organelle to determine labile zinc localization in the subcellular organelle.

17. The method according to claim 16, further comprising:

(d) repeating steps (b) and (c) at determined time intervals and comparing obtained super-resolution imaging data obtained at the determined time intervals to track a change in labile zinc localization in the subcellular organelle over time.

18. The method according to claim 16, wherein the super-resolution imaging is selected from the group consisting of structured illumination microscopy (SIM), stimulated emission depletion (STED) microscopy, ground state depletion (GSD) microscopy, photo-activated localization microscopy (PALM), and stochastic optical reconstruction microscopy (STORM).

19. The method according to claim 18, wherein the super-resolution imaging is SIM and has a spatial resolution peak of about 100 nm.

20. The method according to claim 18, wherein imaging data obtained from the super-resolution imaging is correlated with morphological features of subcellular organelles selected from the group consisting of mitochondrial rod shapes, mitochondrial cristae, punctate lysosomes, and reticular endoplasmic reticulum to detect, visualize, or track labile zinc localization in subcellular organelles.

21. The method according to claim 16, wherein the living cell is in situ or in vivo.

22. The method according to claim 16, wherein the at least one morphological feature of the subcellular organelle is selected from the group consisting of shape, structure, size, and combinations thereof.

23. The method according to claim 16, wherein the NapBu-BPEA does not comprise a specific subcellular organelle-targeting group and wherein the method does not comprise co-localization with a second dye.

* * * * *